(12) United States Patent
Hong et al.

(10) Patent No.: US 9,040,694 B1
(45) Date of Patent: May 26, 2015

(54) COMPOUNDS AND METHODS USEFUL FOR DIRECTING STEM CELL DIFFERENTIATION

(71) Applicant: Vanderbilt University, Nashville, TN (US)

(72) Inventors: Charles C. Hong, Nolensville, TN (US); Corey R. Hopkins, Nolensville, TN (US); Antonis K. Hatzopoulos, Nashville, TN (US); Craig W. Lindsley, Brentwood, TN (US); Jijun Hao, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/337,412

(22) Filed: Jul. 22, 2014

Related U.S. Application Data

(62) Division of application No. 12/537,037, filed on Aug. 6, 2009, now Pat. No. 8,822,684.

(51) Int. Cl.
| | |
|---|---|
| *A61K 31/5377* | (2006.01) |
| *C07D 413/14* | (2006.01) |
| *C12N 5/0735* | (2010.01) |
| *G01N 33/50* | (2006.01) |
| *C07D 487/04* | (2006.01) |

(52) U.S. Cl.
CPC .......... *C12N 5/0606* (2013.01); *G01N 33/5026* (2013.01); *C07D 487/04* (2013.01); *C12N 2501/40* (2013.01); *A61K 31/5377* (2013.01); *C07D 413/14* (2013.01)

(58) Field of Classification Search
CPC . A61K 31/5377; C07D 413/14; C07D 487/04
USPC .......................................... 544/281, 117, 122
See application file for complete search history.

(56) References Cited

U.S. PATENT DOCUMENTS

| | | | | |
|---|---|---|---|---|
| 8,507,501 | B2 * | 8/2013 | Yu et al. ...................... | 514/259.3 |
| 8,822,684 | B1 * | 9/2014 | Hong et al. ................... | 544/281 |

OTHER PUBLICATIONS

Cuny, D.G. et al., Structure-activity relationship study of bone morphogenetic protein (BMP) signaling inhibitors. Bioorganic & Medicinal Chemistry Letter, 2008; 18:4388-4392.
Daniels, R.N. et al., Microwave-assisted protocols for the expedited synthesis of pyrazolo [1,5-a] and [3,4-d] pyrimidines. Tetrahedron Letters, 2008; 49:305-310.
Fraley, M.E. et al., Synthesis and initila SAR studies of 3,6-disubstituted pyrazolo[1,5-a]pyrimidines: a new class of KDR kinase inhibitors. Bioorganic & Medicinal Chemistry Letters 2002; 12:2767-2770.
Fraley, M.E. et al., Optimization of a pyraxolo [1,5-a]pyrimidine class of KDR kinase inhibitors: improvements in physical properties enhance cellular activity and pharmacokinetics. Bioorganic & Medicinal Chemistry Letters 2002; 12:3537-3541.
Hao, J. et al., Dorsomorphin, a selective small molecule inhibitor of the BMP signaling, promotes cardiomyogenesis in embryonic stem cells. PLoS One 2008; 3:e2904.
Hao, J. et al., In Vivo Structure—Activity Relationship Study of Dorsomorphin Analogues Identifies Selective VEGF and BMP Inhibitors, ACS Chemical Biology, vol. 5, No. 2, 2010.
Hong, C.C., et al., Role of Crosstalk Between Phosphatidylinositol 13-Kinase and Extracellular Signal-Regulated Kinase Pathways in Artery-Vein Specification. Circulation Research 2008; 103:573-579.
Hong, C.C. et al., Large-scale small molecule screen using zebrafish embryos, in Cell-based Assays in High-Throughput Screening, Methods in Molecular Biology 2009; 486:43-55 (Clemons PA, Tolliday NJ, Wagner BK, eds.), Totowa, NJ, Humana Press.
Hong, C.C. et al., Applications of small molecule BMP inhibitors in physiology and disease. Cytokines and Growth Factor Reviews, 2009, 409-418.
Hong, C.C. et al., Cardiac Induction by Dorsomorphin, a selective small molecule inhibitor of BMP signaling. Circulation Research 2008; 103:e44.
Kaplan, F.S. et al., Early mortality and cardiorespiratory failure in patients with fibrodysplasia ossificans progressiva. Journal of Bone & Joint Surgery, 2009 (in press).
Wada, T. et al., Highly efficient differentiation and enrichment of spinal motor neurons derived from human and monkey embryonic stem cells. PLoS ONE 2009; 4:e6722.
Wang, J. et al., Selective modulation of TLR4-activated inflammatory responses by altered iron homeostasis. Journal of Clinical Investigation, 2009; 119:3322-3328.
Yu, P.B. et al., Dorsomorphin inhibits BMP signals required for embryogenesis and iron metabolism. Nature Chemical Biology 2008; 4:33-41.
Yu, P.B. et al., BMP type II receptor is required for BMP-mediated growth arrest and differentiation in pulmonary artery smooth muscle cells. J. Biol. Chem. 2008; 283-3877-3888.

(Continued)

*Primary Examiner* — Rebecca Anderson
(74) *Attorney, Agent, or Firm* — Stites & Harbison PLLC; Mandy Wilson Decker

(57) ABSTRACT

The presently-disclosed subject matter relates to compounds of the formula:

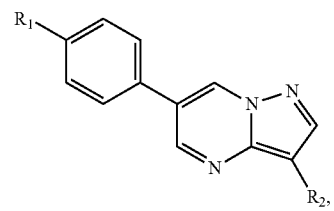

and methods for use thereof. The presently-disclosed subject matter relates methods of selectively differentiating a stem cell, and methods of screening for compounds useful for enhancing terminal differentiation of committed cardiac progenitor cells.

16 Claims, 8 Drawing Sheets

(56) References Cited

OTHER PUBLICATIONS

Yu, P.B. et al., BMP type I receptor inhibition reduces heterotopic ossification. Nature Medicine 2008; 14:1363-1369.
Boyle, A.J., Stem Cell Therapy for Cardiac Repair: Ready for the Next Step, Circulation 2006; 114; 339-352.
Mendez-Ferrer, S., et al., Resident progenitors and bone marrow stem cells in myocardial renewal and repair, Nature Clinical Practice—Cardiovascular Medicine, Mar. 2006, vol. 3, Supplement 1, pp. S83-S89.
Kattman, S. J. et al., Multipotent Flk-1+ Cardiovascular Progenitor Cells Give Rise to the Cardiomyocyte, Endothelial, and Vascular Smooth Muscle Lineages, Developmental Cell 11, 723-732, Nov. 2006.

* cited by examiner

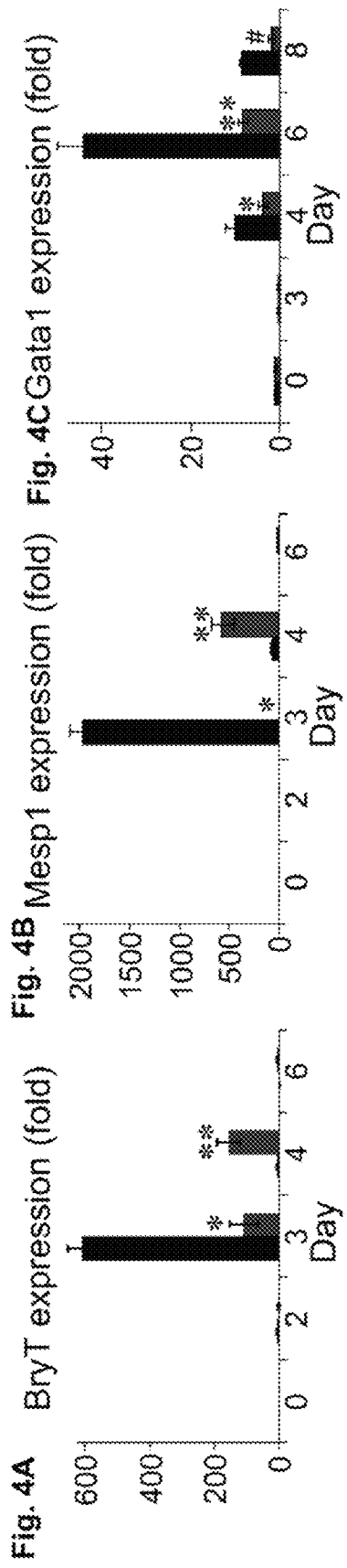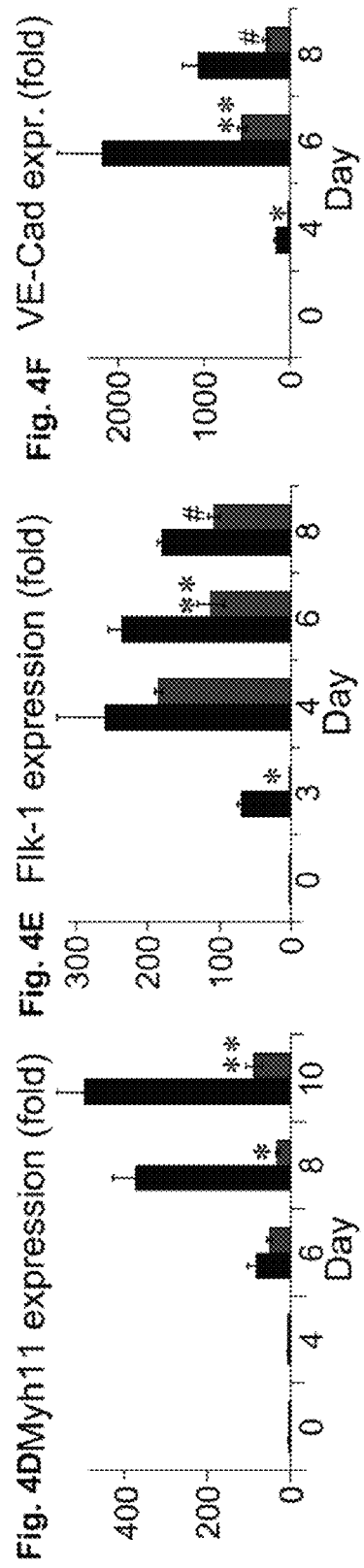

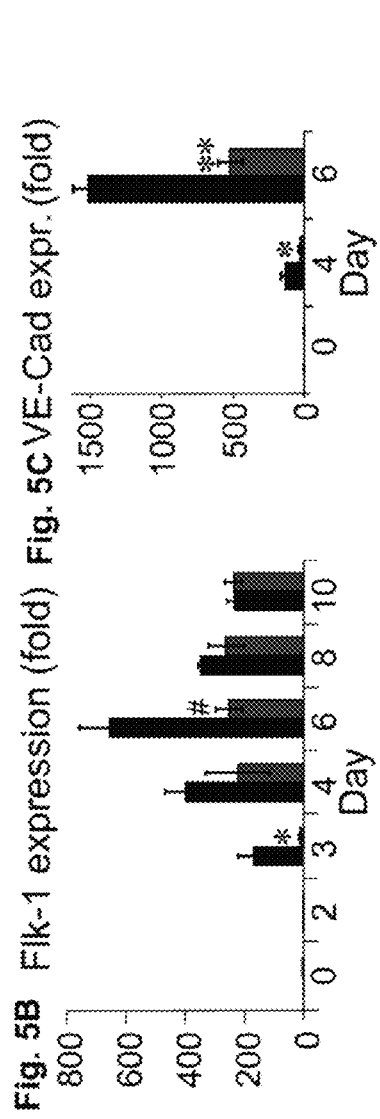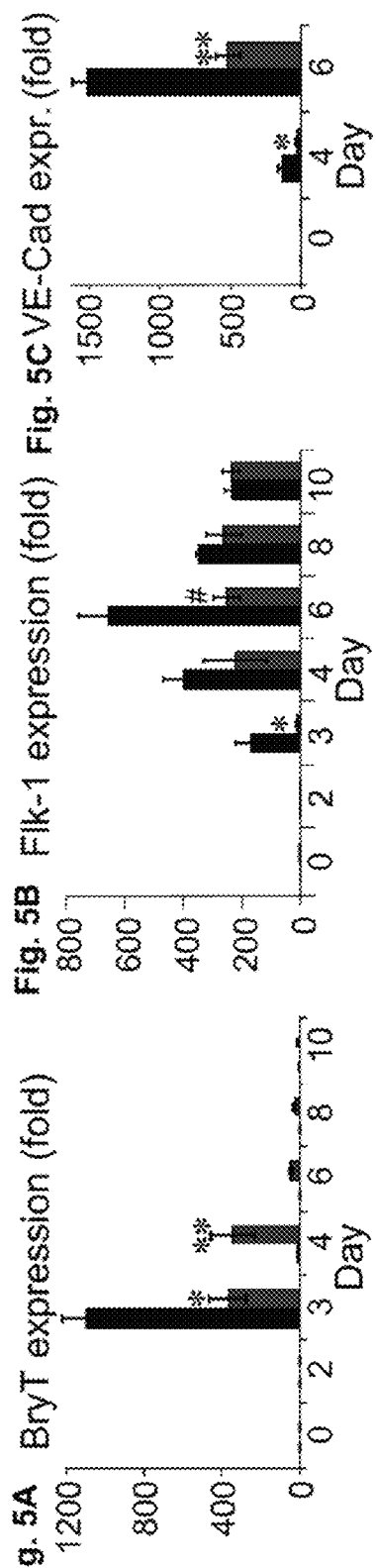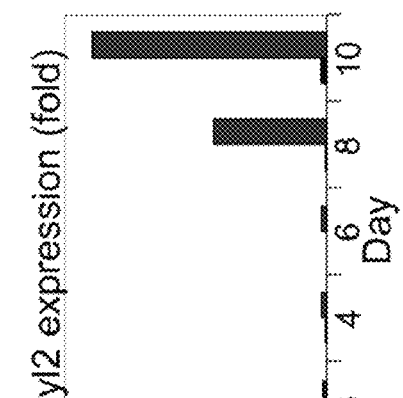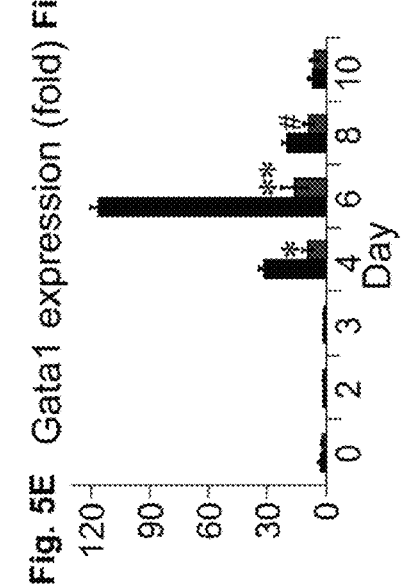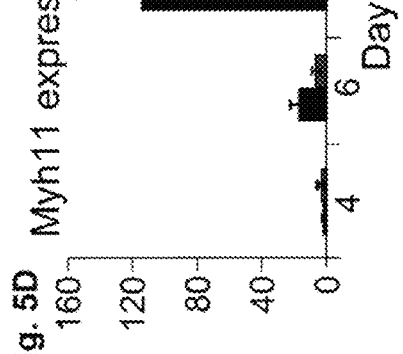

COMPOUNDS AND METHODS USEFUL FOR DIRECTING STEM CELL DIFFERENTIATION

RELATED APPLICATIONS

This application claims priority from and is a division of U.S. patent application Ser. No. 12/537,037, filed Aug. 6, 2009, now allowed, the entire disclosure of which is incorporated herein by this reference.

GOVERNMENT INTEREST

Subject matter described herein was made with U.S. Government support under Grant Numbers 5K08HL081535-02 and 1R01HL083958-01 awarded by the National Institutes of Health. The government has certain rights in the described subject matter.

TECHNICAL FIELD

The presently-disclosed subject matter relates methods and compositions for directing stem cell differentiation. In particular, the presently-disclosed subject matter relates to methods and compositions for directing stem cell differentiation to generate cardiomyocytes. The presently-disclosed subject matter further relates to bone morphogenetic protein (BMP) Inhibitors.

INTRODUCTION

Pluripotent stem cells, which are capable of self-renewal and differentiation into multiple tissue types, show enormous potential as a source of cells to replace damaged adult tissues.[1,2] For example, functional cells derived from pluripotent stem cells might one day be used for replacing damaged heart muscle or dead neurons to improve the outcomes of millions of patients with heart failure and neurodegenerative conditions. Nonetheless, harnessing the regenerative potential of stem cells faces numerous formidable challenges. One such challenge is to develop reliable methods of directing differentiation of stem cells to generate desired cell types. One promising approach to achieve directed stem cell differentiation for therapeutic purposes involves manipulation of known master signaling pathways involved in cell fate specification during embryonic development.

One of such "master" pathways for cell fate determination is the bone morphogenetic protein (BMP) signaling pathway. In addition to embryonic pattern formation and organogenesis, the BMP pathway plays a key role in a number of disease processes. Moreover, while a variety of methods can be employed to modulate the key developmental pathways, selective small molecule modulators in particular are valuable for directing differentiation of stem cells.[3,4] For example, a small molecule that can block the effects of multiple BMP ligand subtypes and receptors might be useful in contexts where the specific cocktail of BMPs and cognate BMP antagonists at play is difficult to pin point. Moreover, small molecules permit exquisite temporal control over BMP signaling. This can be useful for manipulation of BMP signaling in complex biological contexts like in vitro embryonic stem (ES) cell differentiation, where BMP signals are required at multiple time points to regulate a number of diverse developmental events.[2,4,5,6,7] Thus, small molecule inhibitors of BMP signaling are valuable for directing differentiation of pluripotent stem cells toward desired cell types, like neurons, endocrine cells, and cardiomyocytes.

With regard to cardiomyocytes, replacement of damaged heart muscle with cells derived from either exogenous pluripotent stem cells or endogenous local progenitor cells offers enormous hope to improve the outcome of five million Americans afflicted with heart failure, whose current treatments remain largely palliative.[8] Feasibility of cell-based therapy for heart diseases is supported by growing evidence that the heart has some, albeit limited, regenerative capacity after injury.[9] While the source of cells responsible for cardiac repair has not yet been fully determined, select cells resident in the heart appear to possess limited capacity to proliferate and to differentiate into cardiomyocytes.[10,11,12,13] Moreover, pre-clinical studies in animal models and small clinical trials have shown that stem cells transplanted in an infarcted myocardium could enhance cardiac recovery.[8,14,15,16,17,18,19,20]

Despite recent advances, however, present collective experience suggests that the benefits of straightforward cell therapy to treat heart disease are modest, the generation of new cardiac tissue is minimal, and the mechanism of beneficial action of cell therapy remains largely unknown.[21,22,23] Major impediments to harnessing the regenerative potential of stem cells include the poor long-term survival of engrafted cells, the limited potential of pluripotent stem cells to differentiate into functional cardiomyocytes, and the lack of pharmaceutical agents to aid in regenerative medicine.[24] In vitro differentiation of pluripotent ES cells provides an excellent framework for exploring strategies to augment the cardiomyogenic potential of stem cells.[3,4,5] Presently, ES cells remain the only well-characterized stem cell type reliably shown to be capable of differentiating into cardiomyocytes both in vitro and in vivo.[2,25,26,27,28,29,30]

While the mechanisms by which myocardial cells are generated from ES cells are still poorly understood, recent studies indicate that cardiomyogenesis occurs largely through a stepwise progression of lineage commitment, rather than simple induction of uncommitted cells by "cardiogenic" conditions.[31,32] Perhaps because of this step-wise progression of lineage commitment and because ES cell differentiation occurs largely in a stochastic manner in present culturing conditions, transplantation of "naïve" ES cells into the heart incurs the risk of teratoma development.[33] Therefore, successful approaches to control and promote development of cardiomyocytes from pluripotent stem cells will likely involve modulation of signaling pathways involved in embryonic cell-fate specification, such as the bone morphogenetic protein (BMP) signaling pathway.[5] Since in vitro cardiac differentiation of cell types (cord blood stem cells, bone marrow-derived CD34+ cells, endothelial progenitor cells, cardiac side population cells, resident cardiac stem cells, and mesenchymal stem cells) used in transplantation studies takes up to several weeks for cardiac differentiation, compounds that can accelerate and/or augment cardiac differentiation in these stem cell models would greatly enhance stem cell research and open up new potential avenues to boost therapeutic efficacy of stem cells. Accordingly, there remains a need in the art for compositions and methods that will not only selectively differentiate stem cells into cardiomyocytes, but will also accelerate and/or augment cardiac differentiation in these stem cells.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compounds useful for selectively differentiating stem cells. The presently-disclosed subject matter further includes methods of selectively differentiating a stem cell. The presently-disclosed subject matter further includes methods of screening for compounds useful for enhancing terminal differentiation of committed cardiac progenitor cells.

In some embodiments, the compound of the presently-disclosed subject matter have utility as a bone morphogenetic protein (BMP) inhibitor. In some embodiments, the compound has utility for use with a method as described herein. In some embodiments, the compound is a compound of the formula:

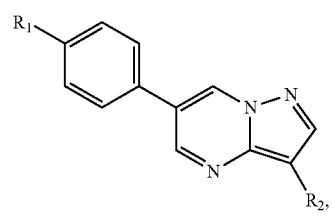

wherein $R_1$ is selected from the group consisting of

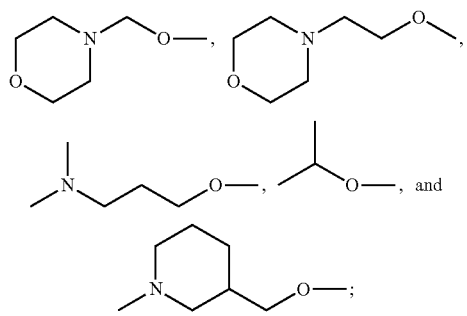

and $R_2$ is selected from the group consisting of

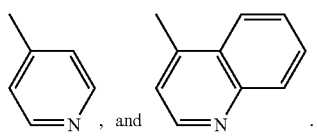

In some embodiments, the compound be a compound of one of the following formulae:

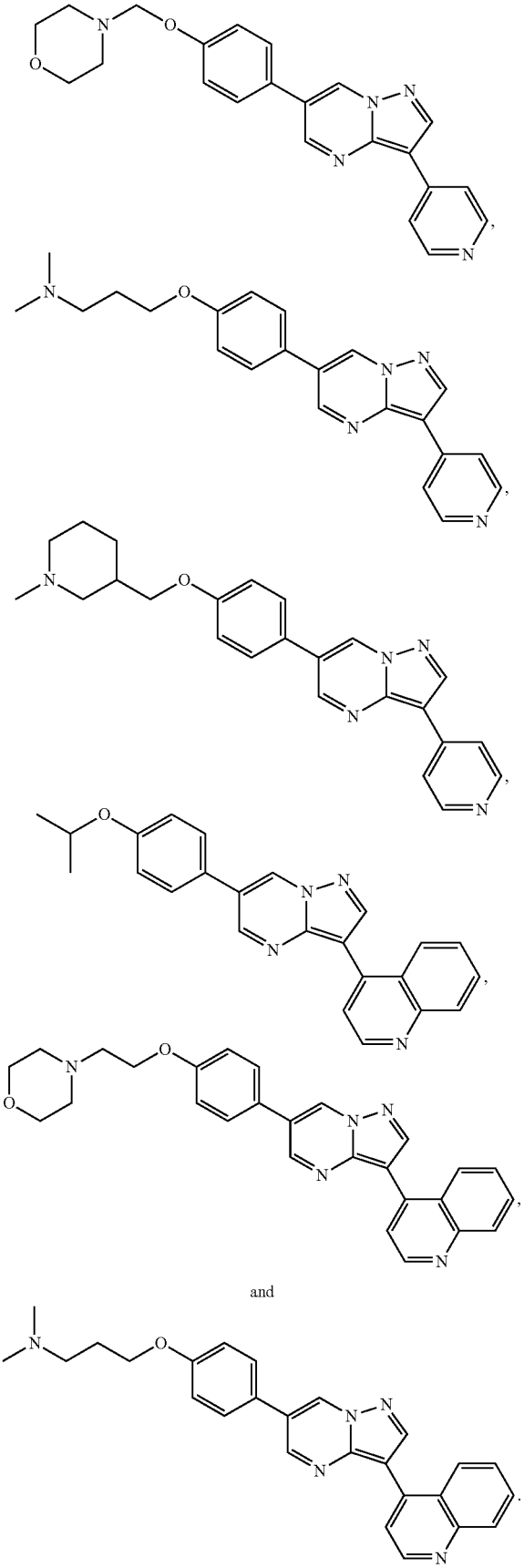

In some embodiments, a method of selectively differentiating a stem cell includes: providing the stem cell; and contacting the stem cell with an effective amount of a compound of the formula,

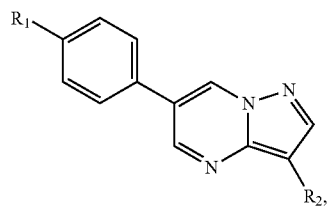

wherein R₁ is selected from the group consisting of

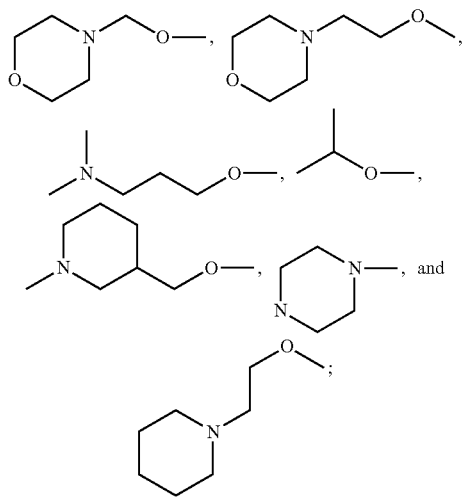

and R₂ is selected from the group consisting of

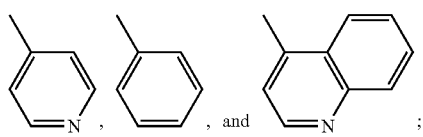

and wherein the stem cell becomes differentiated into a cardiomyocyte.

In some embodiments, the method of selectively differentiating a stem cell includes contacting the stem cell with an effective amount of a compound selected from the group consisting of:

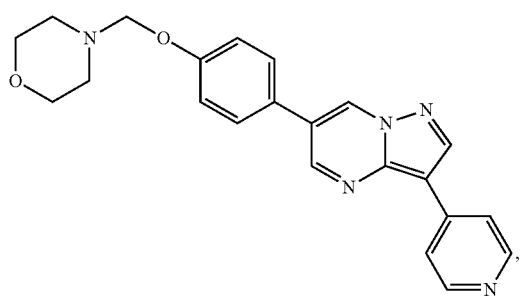

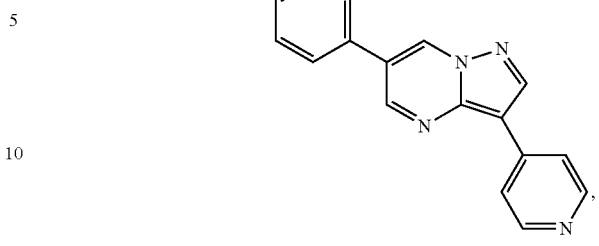

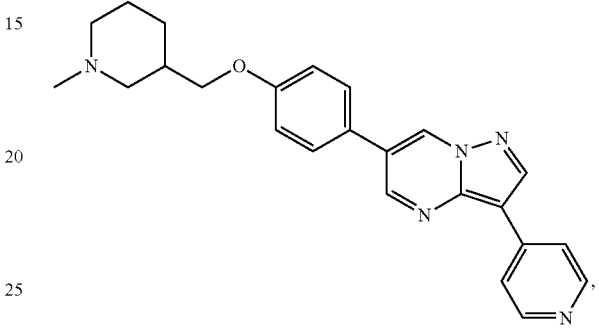

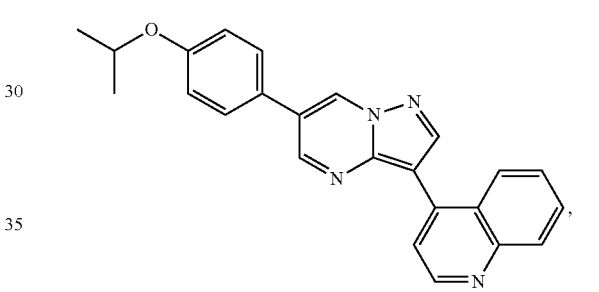

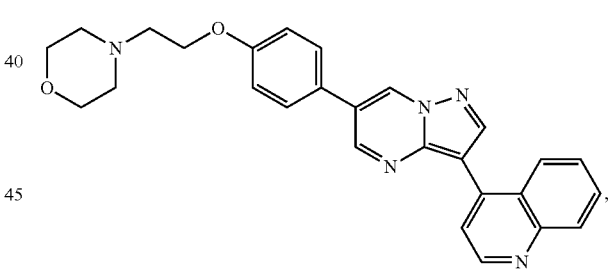

and

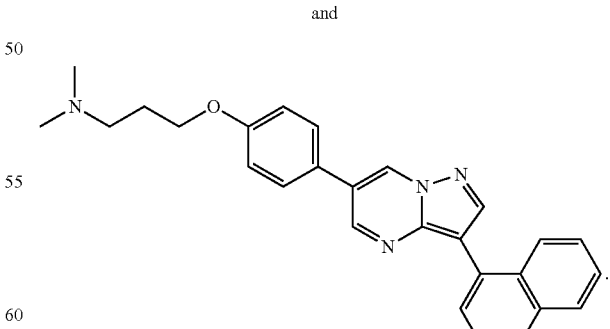

In some embodiments, the method of selectively differentiating a stem cell includes contacting the stem cell with an effective amount of a compound selected from the group consisting of:

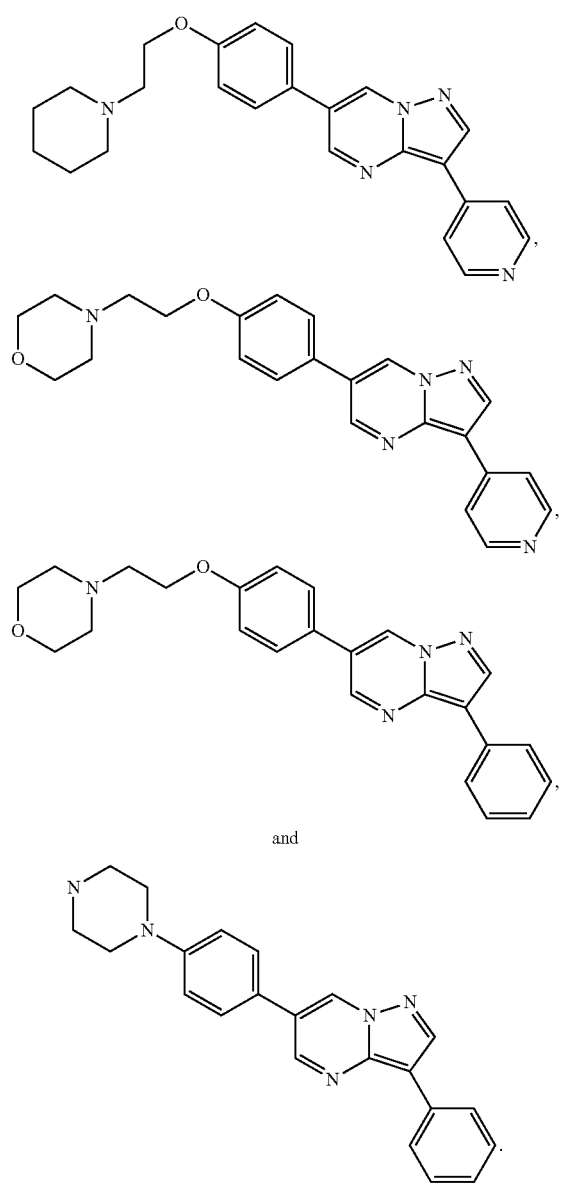

and

In some embodiments of the method of selectively differentiating a stem cell, the compound is an inhibitor of Bone Morphogenetic Protein (BMP) signaling. In some embodiments, contacting the cells with the compound causes the cells to exhibit at least one indicator of cardiomyogenesis. In some embodiments, the at least one indicator of cardiomyogenesis is selected from: fluorescence, beating cells, and expression of at least one cardiac-specific gene. In some embodiments, the at least one cardiac-specific gene is selected from: Nkx2.5, Troponin T, Myh6, Myl2, Myl7, and Mybpc3. In some embodiments, the at least one indicator of cardiomyogenesis is beating cells and, the beating cells are first observed from about day 6 to about day 12.

In some embodiments of the method of selectively differentiating a stem cell, the stem cell is an embryonic stem cell. In some embodiments, the stem cell is a human embryonic stem cell.

In some embodiments of the method of selectively differentiating a stem cell, the method also includes: providing a second compound that enhances terminal differentiation of committed cardiac progenitor cells; and contacting the stem cell with the second compound.

In some embodiments, a method screening for a compound useful for enhancing terminal differentiation of committed cardiac progenitor cells includes: providing a first pluripotent stem cell and a second pluripotent stem cell; contacting the first and second pluripotent stem cells with an effective amount of a first compound of the formula,

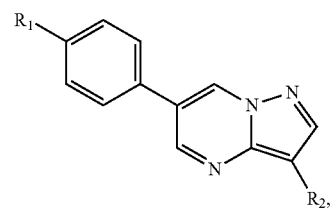

wherein $R_1$ is selected from the group consisting of

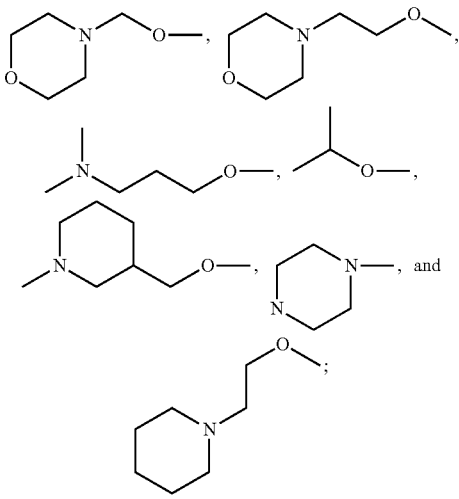

and $R_2$ is selected from the group consisting of

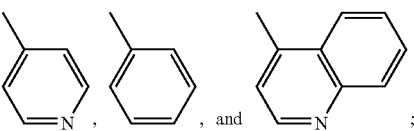

contacting the second cells with a test compound; identifying at least one indicator of cardiomyogenesis exhibited by the first cells and the second cells; comparing the appearance of the at least one indicator of cardiomyogenesis exhibited by the first cells to the appearance of the at least one indicator of cardiomyogenesis exhibited by the second cells; and identifying the test compound as a compound useful for enhancing terminal differentiation of committed cardiac progenitor cells if the appearance of the at least one indicator of cardiomyogenesis in the second cells is accelerated and/or augmented as compared to the appearance of the at least one indicator of cardiomyogenesis in the first cells.

BRIEF DESCRIPTION OF THE DRAWINGS

FIG. 4A is a bar graph depicting BryT expression in mouse ES cells over time, following treatment with DM from day 0 to day 1 of differentiation.

FIG. 4B is a bar graph depicting Mesp1 expression in mouse ES cells over time, following treatment with DM from day 0 to day 1 of differentiation.

FIG. 4C is a bar graph depicting Gata1 expression in mouse ES cells over time, following treatment with DM from day 0 to day 1 of differentiation.

FIG. 4D is a bar graph depicting Myh11 expression in mouse ES cells over time, following treatment with DM from day 0 to day 1 of differentiation.

FIG. 4E is a bar graph depicting Flk-1 expression in mouse ES cells over time, following treatment with DM from day 0 to day 1 of differentiation.

FIG. 4F is a bar graph depicting VE-Cad expression in mouse ES cells over time, following treatment with DM from day 0 to day 1 of differentiation.

FIG. 5A is a bar graph depicting BryT expression in mouse ES cells over time, following treatment with DM from day −3 to day 2 of differentiation.

FIG. 5B is a bar graph depicting Flk-1 expression in mouse ES cells over time, following treatment with DM from day −3 to day 2 of differentiation.

FIG. 5C is a bar graph depicting VE-Cad expression in mouse ES cells over time, following treatment with DM from day −3 to day 2 of differentiation.

FIG. 5D is a bar graph depicting Myh11 expression in mouse ES cells over time, following treatment with DM from day −3 to day 2 of differentiation.

FIG. 5E is a bar graph depicting Gata1 expression in mouse ES cells over time, following treatment with DM from day −3 to day 2 of differentiation.

FIG. 5F is a bar graph depicting Myl2 expression in mouse ES cells over time, following treatment with DM from day −3 to day 2 of differentiation.

DESCRIPTION OF EXEMPLARY EMBODIMENTS

Figure 1:
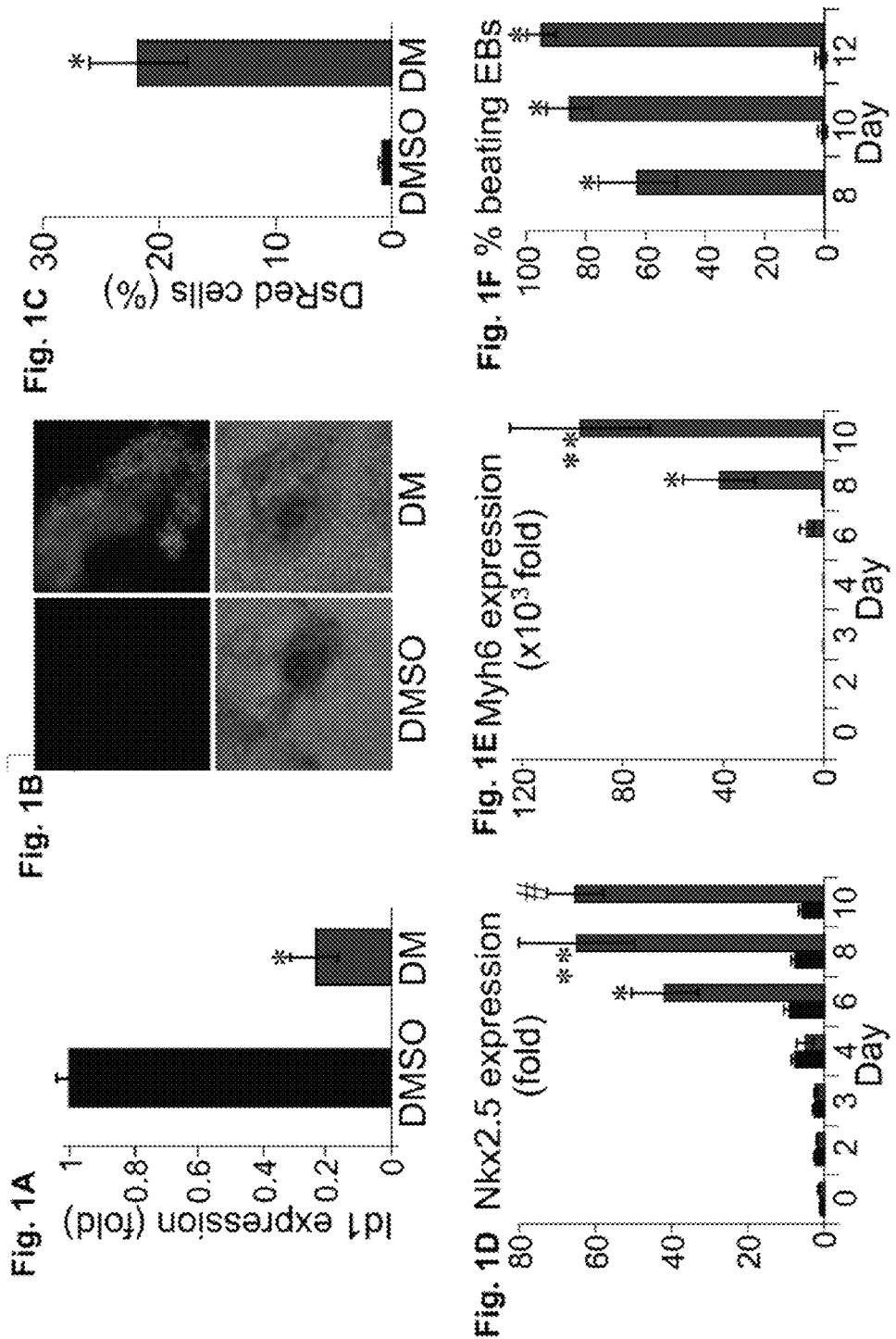
FIG. 1A is a bar graph depicting Id1 expression in mouse ES cells treated with dorsomorphin (DM).
FIG. 1B includes red fluorescent images (upper panels) and bright field images (lower panels) of mouse ES cells treated with DM.
FIG. 1C is a bar graph depicting the percentage of DsRed mouse ES cells after treatment with DM.
FIG. 1D is a bar graph depicting Nkx2.5 expression in mouse ES cells treated with DM.
FIG. 1E is a bar graph depicting Myh6 expression in mouse ES cells treated with DM.
FIG. 1F is a bar graph depicting the percentage of beating embryoid bodies (EB) on differentiation days 8, 10, and 12 of mouse ES cells treated with DM.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the following terms are believed to be well understood by one of ordinary skill in the art, the definitions included in this document are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The presently-disclosed subject matter includes compounds useful for selectively differentiating stem cells. The presently-disclosed subject matter further includes methods of selectively differentiating a stem cell. The presently-disclosed subject matter further includes methods of screening for compounds useful for enhancing terminal differentiation of committed cardiac progenitor cells.

Compounds of the presently-disclosed subject matter will now be described. In some embodiments, the compound has utility as a bone morphogenetic protein (BMP) inhibitor. In some embodiments, the compound has utility for use with a method as described herein.

In some embodiments, the compound of the presently-disclosed subject matter is a compound of the formula:

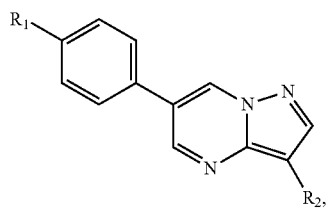

wherein $R_1$ is selected from the group consisting of

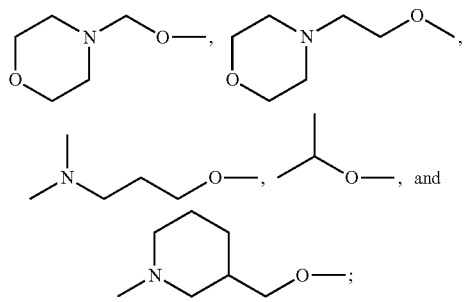

and $R_2$ is selected from the group consisting of

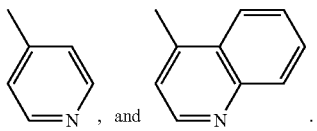

In some embodiments, the compound of the presently-disclosed subject matter is a compound of the formula:

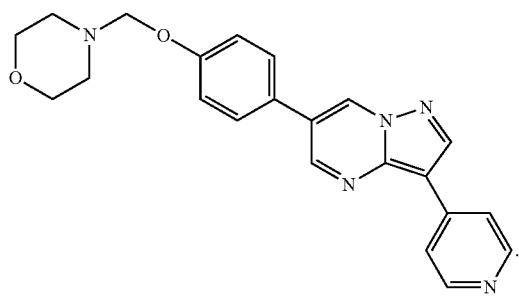 [SMILES: c1cc(-c2cnn3cc(-c4ccc(OCN5CCOCC5)cc4)cnc23)ccn1]

In some embodiments, the compound of the presently-disclosed subject matter is a compound of the formula:

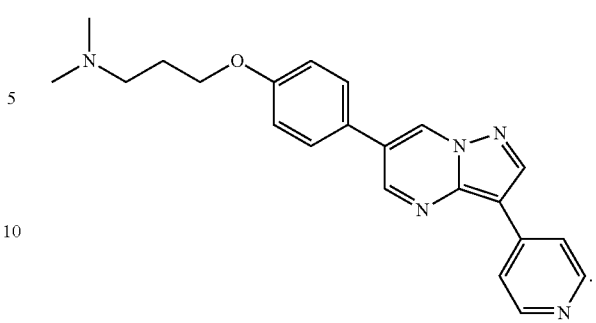

In some embodiments, the compound of the presently-disclosed subject matter is a compound of the formula:

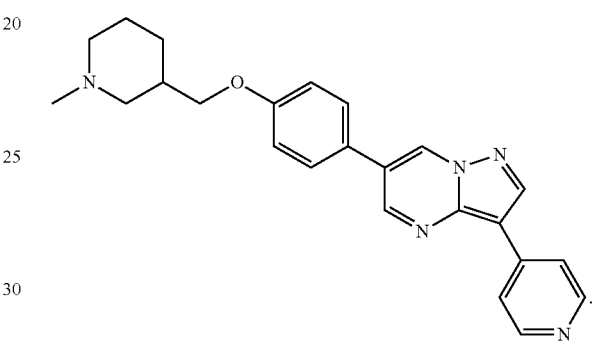

In some embodiments, the compound of the presently-disclosed subject matter is a compound of the formula:

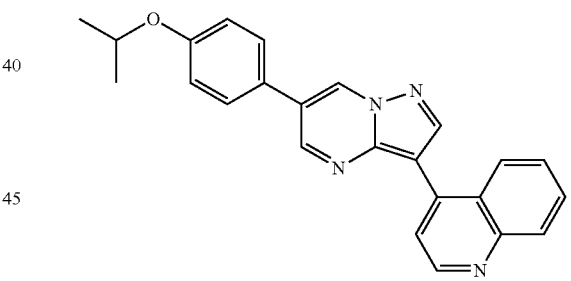

In some embodiments, the compound of the presently-disclosed subject matter is a compound of the formula:

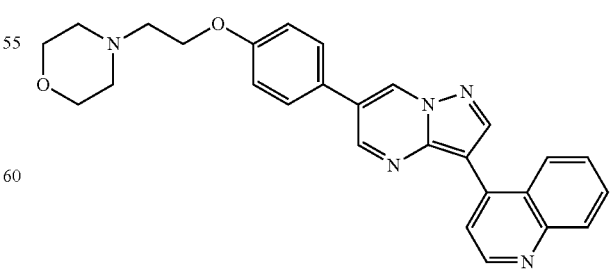

In some embodiments, the compound of the presently-disclosed subject matter is a compound of the formula:

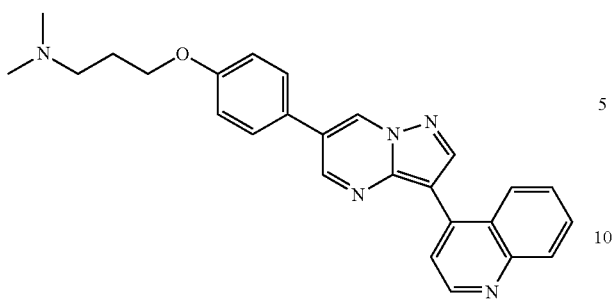

Methods of the presently-disclosed subject matter for selectively differentiating a stem cell will now be described. As used herein, the phrase "selectively differentiating" refers to a process whereby a less specialized cell becomes a desired, specialized cell type. For example, in accordance with the methods of the present invention, a less specialized cell, such as a stem cell, can be induced to undergo differentiation into a more specialized cell type, such as a cardiomyocyte.

The term "stem cell" is commonly defined as a cell which exists for the lifetime of an organism and is able to undergo symmetric and/or asymmetric divisions, to give rise to further stem cells (for preservation of the stem cell pool), or to become differentiated into a cell with a defined life-time and/or organ-specific function. Stem cells are plastic, can become trans-lineaged and/or reprogrammed in different microenvironments formed by supporting cells. Thus, stem cells are distinguishable from other cell types in that they are capable of both differentiating into specialized cells and dividing continuously for long periods of time, making them suitable as cell lines in research and potentially useful in therapeutic treatments. An "embryonic stem cell" or "ES cell" is one type of stem cell and is derived from the inner cell mass of an early stage embryo, known as a blastocyst. Furthermore, ES cells are pluripotent. The term "pluripotent" is used to refer to a stem cell, such as an ES cell, that has the ability to differentiate into any cell or tissue type of the body, including a cardiomyocyte.

As such, pluripotent stem cells show tremendous promise as a versatile source of cells for regenerative therapy. However, because basic mechanisms of lineage specification of pluripotent stem cells are largely unknown, and generating sufficient quantities of desired cell types remains a formidable challenge, small molecules, particularly those that modulate key developmental pathways like the Bone Morphogenetic Protein (BMP) signaling pathway, hold promise to direct differentiation of stem cells toward particular cell types.

It is appreciated that signaling involving the BMP family of ligands plays a diverse role in multiple cellular processes, including cell growth and differentiation. BMP signaling involves binding of a BMP ligand to a type II receptor, which recruits and phosphorylates a type I receptor. These receptors then cause the phosphorylation of a receptor-regulated SMAD (e.g. SMAD1, SMAD5, SMAD8) which then binds to a co-SMAD. The SMAD/co-SMAD complex then enters the nucleus of cells where it plays a role in transcriptional regulation. Furthermore, the natural BMP inhibitor Noggin is capable of promoting mouse stem cell differentiation into cardiomyocytes.

The Applicants have surprisingly discovered that the small molecule dorsomorphin (DM), 6-[4-2-piperidin-1-yl-ethoxy)-phenyl)]-3-pyridin-4-yl-pyrrazolo[1,5-a]-pyrimidine, which was previously identified as a specific inhibitor of BMP signaling,[34] and several other novel small molecules, are capable of differentiating stem cells into cardiomyocytes.

Therefore, in some embodiments of the presently-disclosed subject matter, a method of selectively differentiating a pluripotent stem cell is provided that comprises providing the pluripotent stem cell and contacting it with an effective amount of a compound of the formula

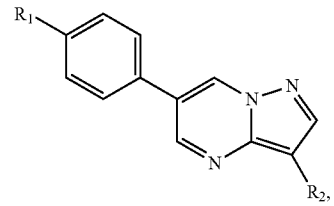

or an analog thereof, wherein $R_1$ is selected from the group consisting of alkyl, branched alkyl, substituted alkyl, aryl, substituted aryl, alkoxy, amino, and dialkylamino; wherein $R_2$ is selected from the group consisting of

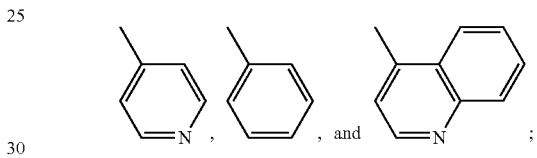

and wherein the pluripotent stem cell becomes differentiated into a cardiomyocyte.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butyryl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes, but is not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "alkoxy" is used herein to refer to a —OZ$^1$ radical, where Z$^1$ is selected from the group consisting of alkyl, substituted alkyl, cycloalkyl, substituted cycloalkyl, heterocycloalkyl, substituted heterocycloalkyl, silyl groups, and combinations thereof as described herein. Suitable alkoxy radicals include, for example, methoxy, ethoxy, benzyloxy, t-butoxy, etc. A related term is "aryloxy" where Z$^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy, and the like.

The term "amino" is used herein to refer to the group —NZ$^1$Z$^2$, where each of Z$^1$ and Z$^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and combinations thereof. Additionally, the amino group can be represented as —N Z$^1$Z$^2$Z$^3$, with the previous definitions applying and Z$^3$ being either H or alkyl.

"Dialkylamino" refers to an —NXX' group wherein each of X and X' is independently an alkyl group as previously described. Exemplary alkylamino groups include ethylmethylamino, dimethylamino, and diethylamino.

When the term "independently selected" is used, the substituents being referred to (e.g., Z$^1$ and Z$^2$), can be identical or different. For example, both Z$^1$ and Z$^2$ can be substituted alkyls, or Z$^1$ can be hydrogen and Z$^2$ can be a substituted alkyl, and the like.

In some embodiments of the presently-disclosed subject matter, R$_1$ is selected from the group consisting of

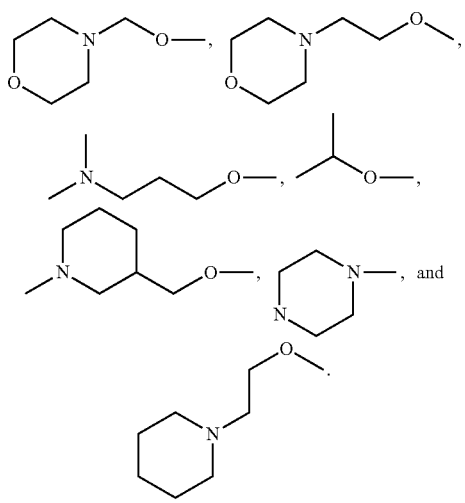

In some embodiments, a method of selectively differentiating a pluripotent stem cell is provided, wherein the pluripotent stem cell is contacted with a compound of the formula,

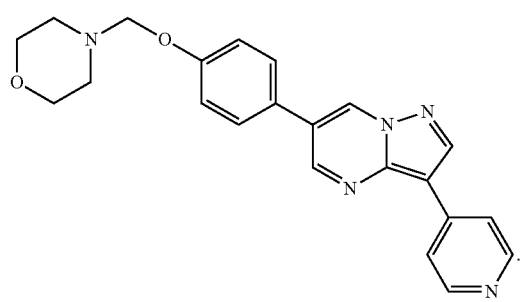 [SMILES: c1cc(-c2cnn3cc(-c4ccc(OCN5CCOCC5)cc4)cnc23)ccn1]

In some embodiments, the compound is a compound of the formula,

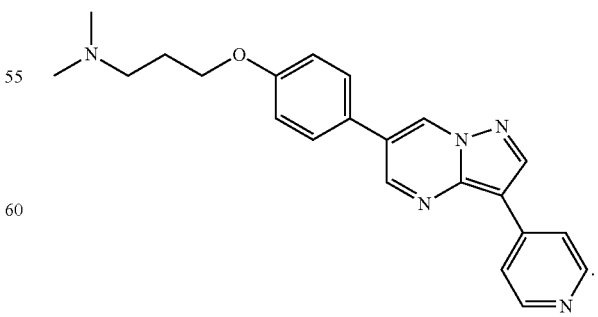

In some embodiments, the compound is a compound of the formula,

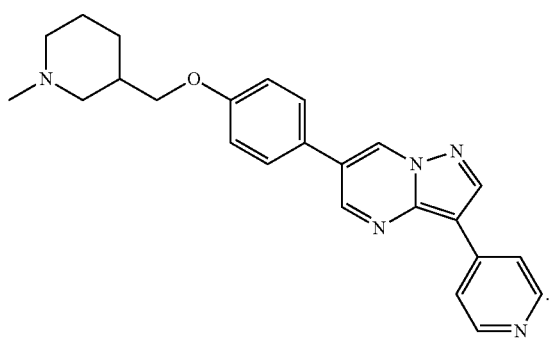 [SMILES: CN1CCCC(COc2ccc(-c3cnc4c(-c5ccncc5)cnn4c3)cc2)C1]

In some embodiments, the compound is a compound of the formula,

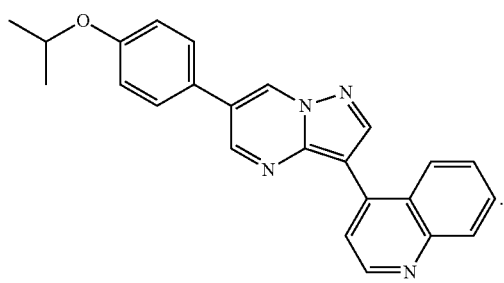 [SMILES: CC(C)Oc1ccc(-c2cnc3c(-c4ccnc5ccccc45)cnn3c2)cc1]

In some embodiments, the compound is a compound of the formula,

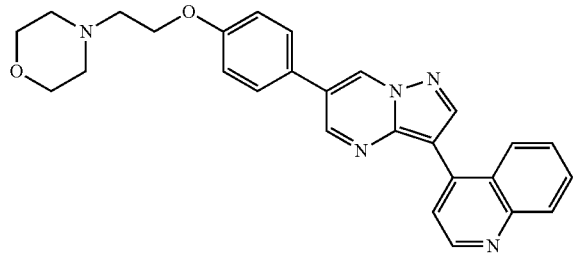

In some embodiments, the compound is a compound of the formula,

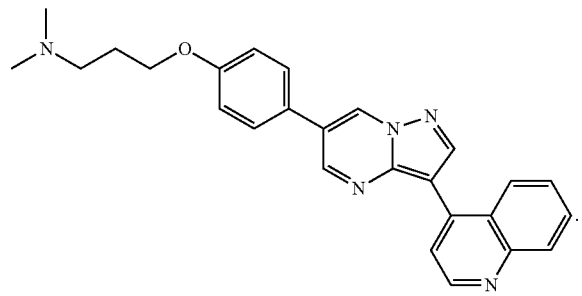 [SMILES: CN(C)CCCOc1ccc(-c2cnc3c(-c4ccnc5ccccc45)cnn3c2)cc1]

In some embodiments, the compound is a compound of the formula,

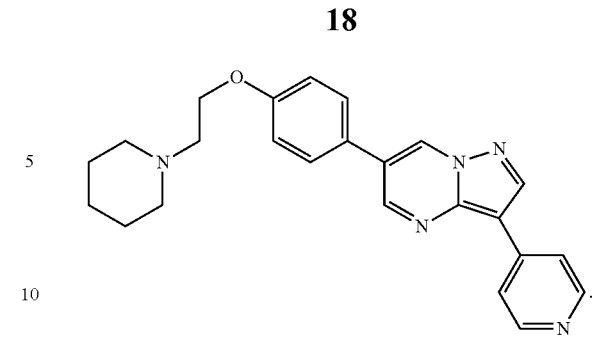

In some embodiments, the compound is a compound of the formula,

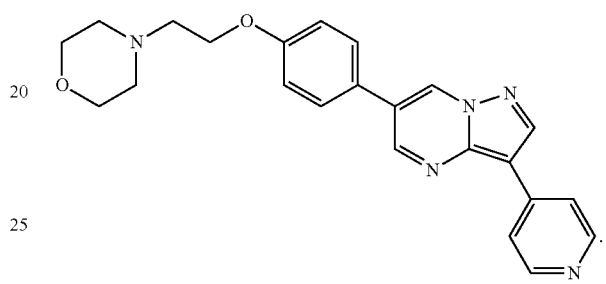

In some embodiments, the compound is a compound of the formula,

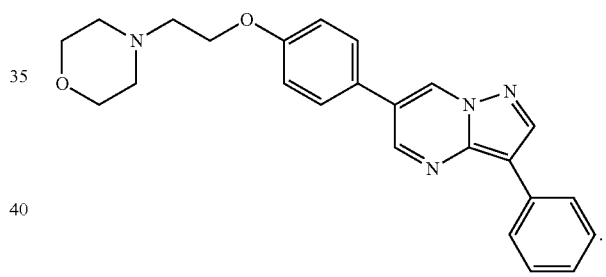

In some embodiments, the compound is a compound of the formula,

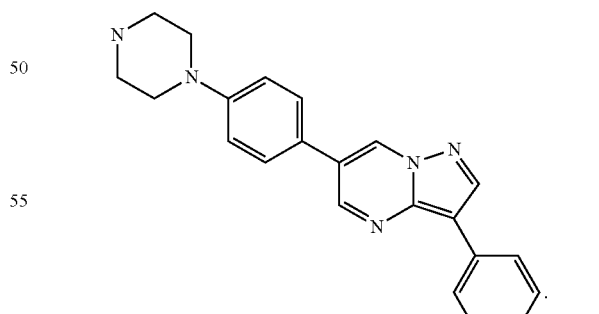

In some embodiments, the compound is an inhibitor of BMP signaling. As used herein, the terms "inhibitor" or "inhibiting" is not meant to require complete inhibition, but refers to a reduction in BMP signaling. Such reduction can be a reduction by at least about 50%, at least about 75%, at least about 90%, or at least about 95% of the BMP signaling in the absence of the inhibitory effect, e.g., in the absence of a compound that is an inhibitor of BMP signaling.

As noted above, in some embodiments, the method includes contacting the pluripotent stem cell with an effective amount of the compound. The term "effective amount" is used herein to refer to an amount sufficient to produce a measurable biological response (e.g. an amount sufficient to cause the pluripotent stem cells to exhibit at least one indicator of cardiomyogenesis). Actual amounts of the compounds can be varied so as to contact the stem cells with an amount of the compound that is effective to achieve the desired response for a particular stem cell and/or application. Determination and adjustment of an effective amount, as well as evaluation of when and how to make such adjustments, will become apparent to those of ordinary skill in the art upon review of this description and can be determined using only routine experimentation.

The term "cardiomyocyte" refers to a cardiac muscle cell. Cardiac muscle is a specialized muscle tissue with some similarities to both smooth and skeletal muscle. It is involuntary and mononucleate as is smooth muscle, although the nucleus is centrally located. The cardiac muscle is striated with microscopically visible myofilaments arranged in structures called sarcomeres. These filaments consist of myosin and actin bundles that slide along each other during the process of contraction and allow for the cells of the cardiac muscle to "beat." The filaments are attached to cell membrane desmosome structures called intercalated discs that also hold adjacent cardiomyocytes together end to end. Cardiomyocytes are endowed with large numbers of mitochondria to provide adenosine tri-phosphate (ATP) energy and with an elaborate sarcoplasmic reticulum that controls $Ca^{++}$ fluxes needed for contraction. Furthermore, cardiomyocytes contain transcriptional regulatory and structural genes which are specific for and preferentially expressed in cardiomyocytes. These transcriptional regulatory and structural genes include, but are not limited to, the transcription factors Nkx2.5, Hand1, Hand2, and sarcomere structural proteins like cardiac alpha myosin heavy chain 6 (Myh6), cardiac alpha myosin heavy chain 7 (Myh7), cardiac myosin light chain 2 (Myl2), myosin light chain 7 (Myl7), cardiac myosin binding protein C (Mybpc3), and Troponin T.

Thus, in some embodiments of the presently-disclosed subject matter, contacting the cells with the compound causes the cells to exhibit at least one indicator of cardiomyogenesis. The phrase "indicator of cardiomyogenesis" is used herein to refer to one or more signs that an ES cell has differentiated into a cardiomyocyte. For example, an indicator of cardiomyogenesis can include, but is not limited to, fluorescence that results from a cell being transfected with a fluorescent gene under the control of a cardiac-specific promoter such as a fluorescent nuclear-DsRed (DsRed-Nuc) gene under the control of the cardiac alpha-myosin heavy chain (α-MHC) promoter, beating cells, or expression of a cardiac-specific gene. Thus, in some embodiments of the presently-disclosed subject matter, the at least one indicator of cardiomyogenesis is selected from: fluorescence, beating cells, and expression of at least one cardiac specific gene. In some embodiments, the at least one cardiac specific gene is selected from: Nkx2.5, Troponin T, Myh6, Myl2, Myl7, and Mybpc3.

In some embodiments, the at least one cardiac marker is beating cells and the beating cells are first observed from about day 6 of differentiation to about day 12 of differentiation. As a non-limiting example, ES cells can be treated with the compounds of the presently-disclosed subject matter for three days and on day 0, embryoid bodies (EB) are generated by methods known to those of ordinary skill in the art. Starting at day 6, EBs can then be microscopically examined for spontaneously beating cardiomyocytes.

Using the method described above for selectively differentiating ES cells into cardiomyocytes, the Applicants have also discovered that the compounds described herein above promote an early step in cardiac lineage specification, rather than inducing terminal differentiation of committed progenitor cells into functional cardiomyocytes. As such, in some embodiments, a method of selectively differentiating a pluripotent stem cell into a cardiomyocyte is provided which comprises contacting the pluripotent stem cell with one of the compounds described herein above, and further comprises providing and contacting the cells with a second compound that enhances terminal differentiation of committed cardiac progenitor cells.

The term "terminal differentiation" is used herein to refer to the final differentiation of a cell into a mature, fully differentiated cell. Usually, terminal differentiation is associated with withdrawal from the cell cycle and cessation of proliferation. The term "progenitor cell" refers to a cell that is committed to a particular cell lineage and which gives rise to fully mature and fully differentiated cells of the cell lineage by a series of cell divisions. As such, the phrase "cardiac progenitor cell" refers to a cell that is committed to a cardiac lineage but is itself not fully mature or fully differentiated.

To "enhance" terminal differentiation, as used herein, means to increase the rate or amount of terminal differentiation of committed cardiac progenitor cells in the presence of a compound described herein above and a second compound, as compared to the amount or rate of terminal differentiation in the absence of the second compound.

Methods of the presently-disclosed subject matter for screening for compounds useful for enhancing terminal differentiation of committed cardiac progenitor cells will now be described.

In some embodiments, a screening method for a compound useful for enhancing terminal differentiation of committed cardiac progenitor cells comprises providing a first stem cell and a second stem cell; contacting the first and second stem cell with an effective amount of a first compound, as described herein; contacting the second cell with a test compound; identifying at least one indicator of cardiomyogenesis exhibited by the first cell and the second cell; comparing the appearance of the at least one indicator of cardiomyogenesis exhibited by the first cell to the appearance of the at least one indicator of cardiomyogenesis exhibited by the second cell; and identifying the test compound as a compound useful for enhancing terminal differentiation of a committed cardiac progenitor cell if the appearance of the at least one indicator of cardiomyogenesis in the second cell is accelerated and/or augmented as compared to the appearance of the at least one indicator of cardiomyogenesis in the first cell. In some embodiments, the first compound is a compound of the formula,

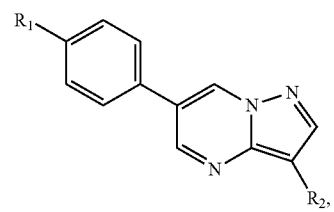

wherein R₁ is selected from the group consisting of alkyl, branched alkyl, substituted alkyl, aryl, substituted aryl, alkoxy, amino, and dialkylamino, and R₂ is selected from the group consisting of

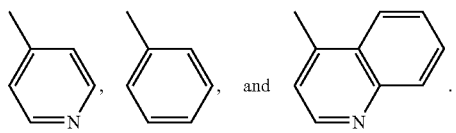

In some embodiments of the presently-disclosed subject matter, R₁ is selected from the group consisting of

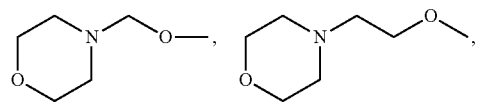

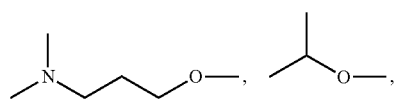

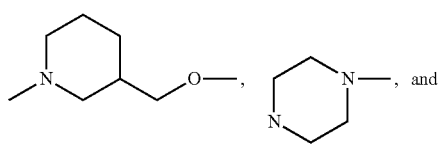

In some embodiments, the first compound is a compound of the formula,

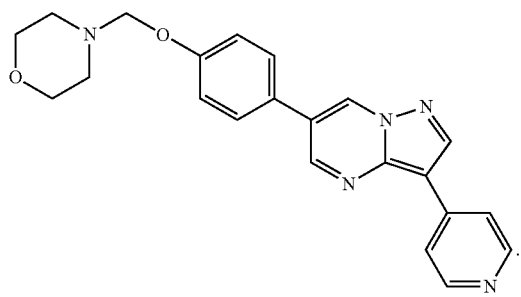 [SMILES: c1cc(-c2cnn3cc(-c4ccc(OCN5CCOCC5)cc4)cnc23)ccn1]

In some embodiments, the first compound is a compound of the formula,

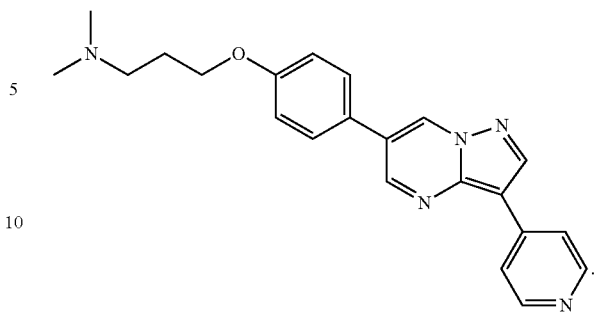

In some embodiments, the first compound is a compound of the formula,

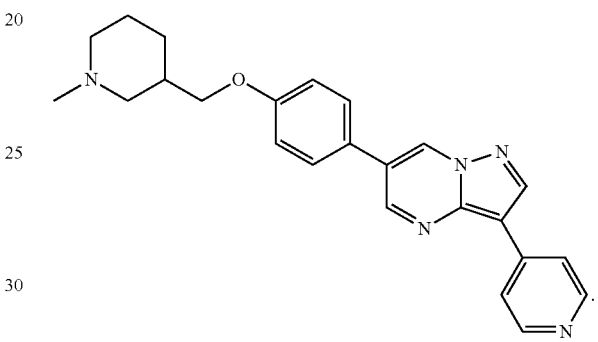

In some embodiments, the first compound is a compound of the formula,

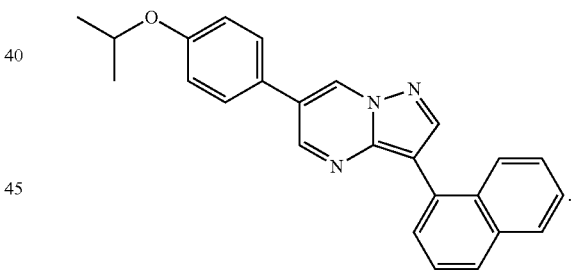

In some embodiments, the first compound is a compound of the formula,

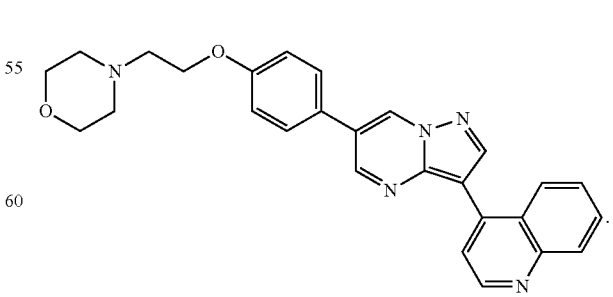

In some embodiments, the first compound is a compound of the formula,

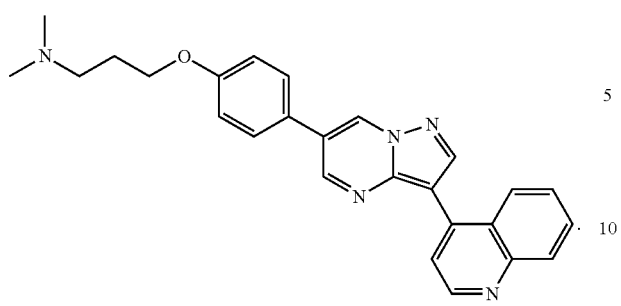

In some embodiments, the first compound is a compound of the formula,

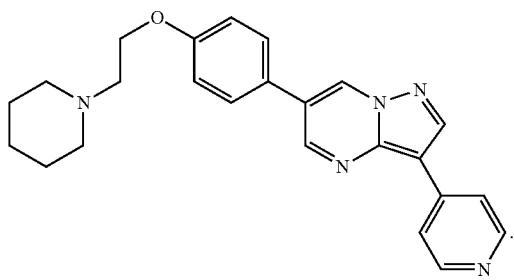 [SMILES: c1cc(-c2cnn3cc(-c4ccc(OCCN5CCCCC5)cc4)cnc23)ccn1]

In some embodiments, the first compound is a compound of the formula,

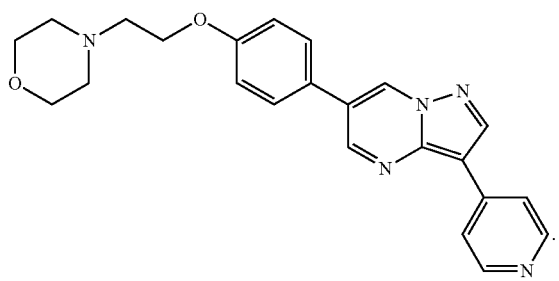 [SMILES: c1cc(-c2cnn3cc(-c4ccc(OCCN5CCOCC5)cc4)cnc23)ccn1]

In some embodiments, the first compound is a compound of the formula,

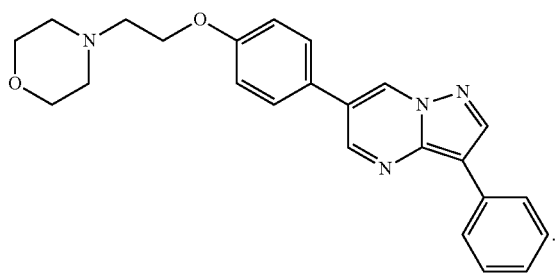 [SMILES: c1ccc(-c2cnn3cc(-c4ccc(OCCN5CCOCC5)cc4)cnc23)cc1]

In some embodiments, the first compound is a compound of the formula,

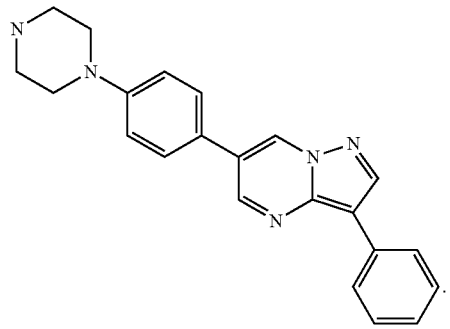 [SMILES: c1ccc(-c2cnn3cc(-c4ccc(N5CCNCC5)cc4)cnc23)cc1]

In some embodiments, the first compound is an inhibitor of BMP signaling.

As used herein, the term "appearance" refers to the detection of one or more indicators of cardiomyogenesis. For example, the appearance can be assessed visually by microscopically examining the cells for fluorescence or beating cells, or the appearance can be assessed by measuring the expression of cardiac-specific genes. Suitable methods for measuring the expression of cardiac-specific genes are known to those skilled in the art and include, but are not limited to, methods such as quantitative real-real time polymerase chain reaction (Q-PCR).

To "accelerate" the appearance of the at least one indicator of cardiomyogenesis means to decrease the amount of time in which an indicator of cardiomyogenesis is first observed in the second cell as compared to the amount of time in which the same indicator is first observed in the first cell. For example, the appearance of fluorescence in the second cell can occur at day 4 of differentiation whereas the appearance of fluorescence can occur in the first cell at day 7 of differentiation.

To "augment" the appearance of the at least one indicator of cardiomyogenesis means to increase the amount of the at least one indicator of cardiomyogenesis observed in the second cell as compared to the amount of the at least one indicator of cardiomyogenesis observed in the first cell. For example, the amount of expression of at least one cardiac-specific gene, such as Nkx2.5, can be increased in the second cell as compared to the first cell.

In some embodiments of the presently-disclosed subject matter, a screening method is provided, wherein the at least one indicator of cardiomyogenesis is selected from: fluorescence, beating cells, and expression of at least one cardiac-specific gene. In some embodiments, the at least one cardiac-specific gene is selected from: Nkx2.5, Troponin T, Myh6, Myl2, Myl7, and Mybpc3. In other embodiments, the at least one indicator of cardiomyogenesis is beating cells, and the beating cells are first observed in the second cell at about day 6.

The presently-disclosed subject matter is further illustrated by the following specific but non-limiting examples. The following examples may include compilations of data that are representative of data gathered at various times during the course of development and experimentation related to the present invention.

EXAMPLES

In a chemical screen for small molecules that disrupt dorsoventral patterning in zebrafish embryos, dorsomorphin (6-[4-(2-Piperidin-1-yl-ethoxy)phenyl]-3-pyridin-4-yl-pyrazolo[1,5-a]pyrimidine), also referred to herein as compound C, was recently identified as a small molecule that selectively inhibits BMP type I receptors.[34,35] Since the natural BMP inhibitor Noggin has been shown to promote mouse ES cell differentiation into cardiomyocytes,[5] the following experimental studies examined whether dorsomorphin could also enhance cardiomyogenesis. The following studies show that dorsomorphin treatment of mouse embryonic stem (ES) cells leads to a strong expansion of the cardiomyocytic lineage in a reproducible manner. In contrast to cardiac induction by Noggin, which required 5 days of treatment begun 3 days before the initiation of ES cell differentiation, dorsomorphin treatment limited to the first 24-hours of differentiation was sufficient for robust cardiac induction. Moreover, the results indicate that inhibition of BMP signaling during the initial stages of differentiation promoted cardiomyogenesis at the expense of endothelial, smooth muscle, and hematopoietic lineages. These findings support a model for the interplay between the myocardial and the hemangioblast lineages, and suggest that blocking BMP signaling early in ES cell differentiation tips the balance in favor of myocardial specification.

Results

Small Molecule BMP Inhibitor, Dorsomorphin, Induces Cardiomyogenesis in Mouse ES Cells.

To gauge cardiomyogenesis, the mouse ES cell line CGR8 was used and was stably transfected with a construct expressing the red fluorescent protein gene fused to a nuclear localization signal (DsRed-Nuc) under the alpha-myosin heavy chain promoter.[36] In this system, α-MHC-expressing cells are marked with red nuclear fluorescence, allowing a visual, quantitative assessment of cardiomyogenesis. The cells were treated with 2 µM dorsomorphin, which effectively blocks BMP-induced SMAD activation[34] but not AMP-activated kinase activity.[37] Dorsomorphin treatment was begun 3 days prior (day −3) to the initiation of embryoid body (EB) formation. Dorsomorphin was added with daily changes of the ES cell media until day 0, when EB formation was initiated in hanging drops containing EB/differentiation medium with an additional dose of dorsomorphin. At day 2 of EB formation, dorsomorphin was washed out. The dorsomorphin vehicle DMSO was used as negative control. This protocol resulted in 76.3% decrease in the BMP-responsive Id1 expression at day 2 of differentiation (FIG. 1A).[37]

Under these conditions, dorsomorphin-treated CGR8 cells formed large areas of spontaneously beating cardiomyocytes that expressed DsRed protein within 12 days of differentiation (FIG. 1B). In contrast, DMSO-treated cells formed small beating areas with few DsRed+ cells. To quantify this effect, dorsomorphin and DMSO-treated cells were stained with DAPI, and, using an automated fluorescence measurement program (Simple PCI), the total number of cells (DAPI+) and the number of DsRed+ cardiomyocytes within individual EBs were estimated. On average, 21.8% of cells in dorsomorphin-treated EBs expressed DsRed, in comparison to 0.8% in controls (FIG. 1C). There was no significant difference in the total number of cells between the two groups, suggesting that dorsomorphin treatment did not impair the growth of differentiating ES cells (Table 1). In the dorsomorphin-treated group, the average number of DsRed+ cells within a 2.4×2-mm field was 473.1, versus 8.5 in controls (Table 1). This represented an approximately 55-fold increase in number of cardiomyocytes with dorsomorphin treatment.

TABLE 1

Dorsomorphin treatment (day −3 to 2) increased numbers of DsRed+ cardiomyocytes without significantly affecting total number of cells.

| | DM | | DMSO | | Fold |
| --- | --- | --- | --- | --- | --- |
| | Ave | SE | Ave | SE | induction |
| DsRed+ | 473.13 | 94.11 | 8.53 | 2.51 | 55.47 |
| DAPI+ | 2221.00 | 387.78 | 1900.55 | 303.04 | |

Dorsomorphin-induced cardiomyogenesis was associated with large increases in expression of several cardiac genes as measured by quantitative real-time PCR (Q-PCR). Compared to controls, dorsomorphin treatment increased expression of the early cardiac marker Nkx2.5 by 11.4-fold (FIG. 1D), the cardiac myosin heavy chain gene (Myh6) by 125-fold (FIG. 1E), and the cardiac myosin light chain 2 (Myl2) by 34.2-fold (FIG. 5F) at day 10 of differentiation.

Figure 6A:
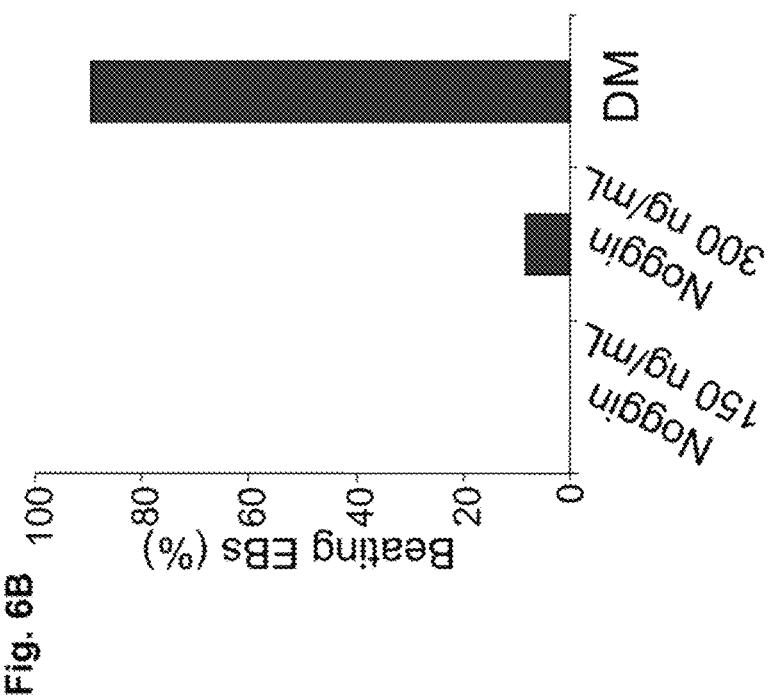
FIG. 6A is a dose response curve illustrating the percentages of beating embryoid bodies (EBs) observed in mouse ES cells following treatment with varying concentrations of DM.

To quantify the frequency of spontaneously beating cardiomyocytes, EB formation was initiated in 96-well microtiter plates. Using this technique, aliquots of 500 ES cells were distributed in uncoated round bottom microtiter plates in differentiation media, and cells allowed to aggregate at the bottom of each well by gravity or by brief centrifugation. EB that contained visible clusters of spontaneously beating cells was recorded as 1 positive well. With this method, only 1.3% of DMSO-treated EBs were found to beat by day 12 of differentiation (FIG. 1F). By contrast, 94.4% of EBs treated with 2 µM dorsomorphin from day −3 to day 2 beat spontaneously by day 12 (FIG. 1F). With this method, a dose-response relationship for cardiac induction by dorsomorphin was determined (FIG. 6A). Dorsomorphin was effective at robustly inducing cardiomyogenesis in the R1 mouse ES cell line, indicating that the procardiogenic effects of dorsomorphin were not restricted to the CGR8 cells (Table 2).

TABLE 2

Frequency of beating EBs from R1 cells.

| | Day 8 (%) | Day 10 (%) | Day 12 (%) |
| --- | --- | --- | --- |
| DM | 42.39 | 85.87 | 91.30 |
| DMSO | 1.05 | 3.15 | 4.21 |

Dorsomorphin Treatment Limited to the First 24-Hours of ES Cell Differentiation is Sufficient for Robust Cardiac Induction.

Figure 2:
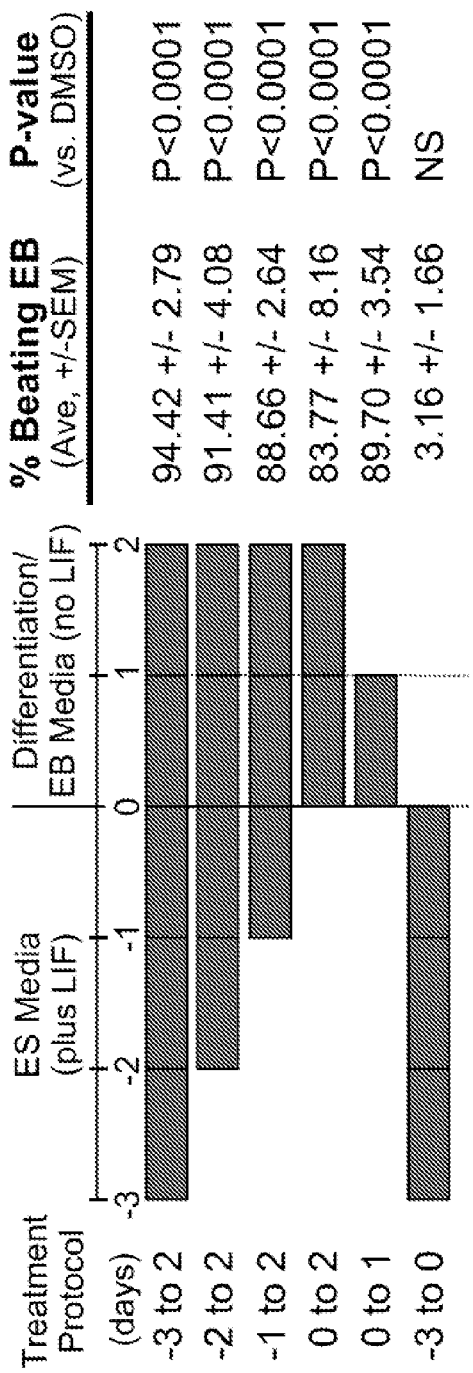
FIG. 2 is a chart depicting various treatments of mouse ES cells with DM and the percentages of beating embryoid bodies (EB) in each treatment.
Figure 6B:
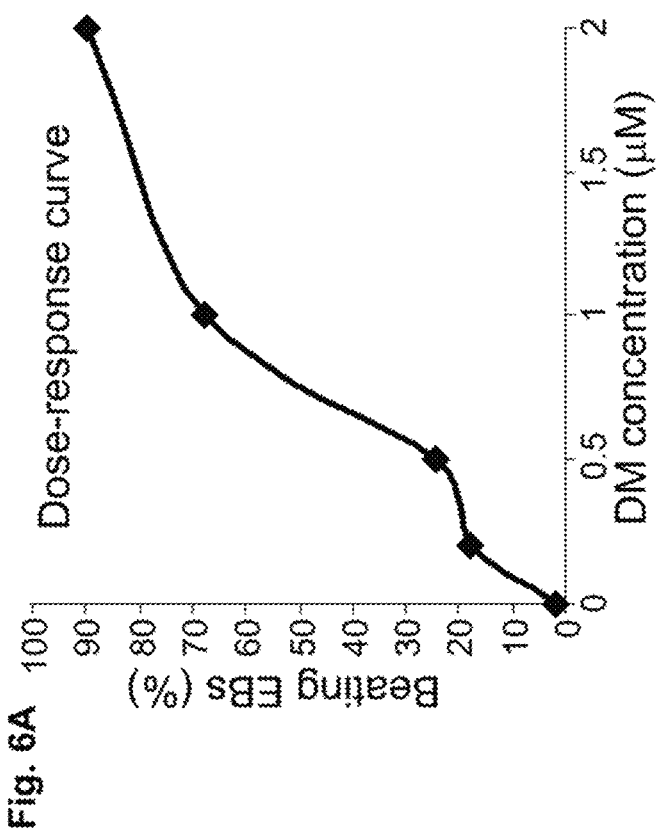
FIG. 6B is a bar graph showing the percentages of beating embryoid bodies (EBs) following treatment with Noggin or dorsomorphin (DM).

The 96-well microtiter format permitted detailed quantitative examination of temporal requirements for robust cardiac induction by dorsomorphin. Treatments starting at day −2 (day −2 to 2), day −1 (day −1 to 2) and day 0 (day 0 to 2) were nearly as effective in promoting cardiac induction as the day −3 to 2 protocol (beating frequencies ranging from 83.8 to 94.4%, (FIG. 2), but dorsomorphin treatment from day −3 to 0 resulted in just 3.2% beating frequency (FIG. 2). Importantly, in contrast to Yuasa et al.,[5] which reported inefficient (<30%) cardiac induction with Noggin treatment from day 0 to 2, and experiments with Noggin (FIG. 6B), dorsomorphin treatments from day 0 to 2 and day 0 to 1 were both very effective in promoting cardiomyogenesis (beating frequencies of 83.8% and 89.7%, respectively; FIG. 2). These results indicate that the critical time window for cardiac induction by dorsomorphin lies within the first 24 hours of ES cell differentiation.

Figure 3A:
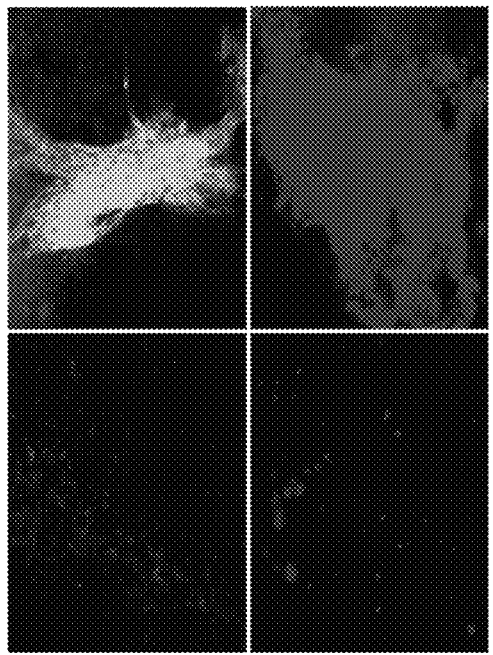
FIG. 3A is a bar graph depicting Id1 expression in mouse ES cells following treatment with DM from day 0 to day 1 of differentiation.
Figure 3B:
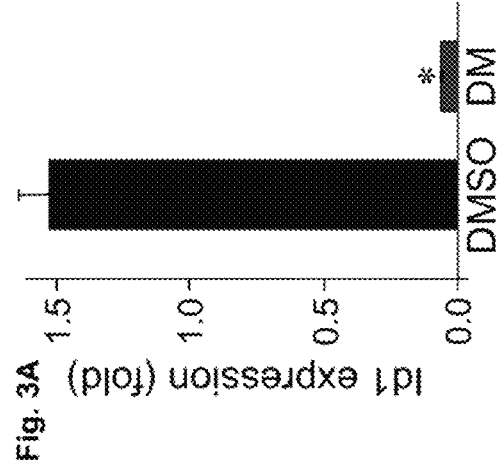
FIG. 3B includes images of mouse ES cells treated with DM from day 0 to day 1 and immunostained for the sarcomeric protein α-actinin at day 10 of differentiation (upper panels) or immunostained for cardiac-specific transcription factor Nkx2.5 (lower panels).
Figure 3C:
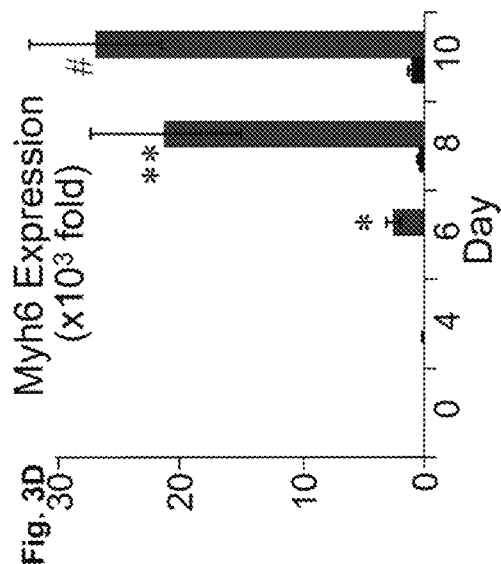
FIG. 3C is a bar graph depicting Nkx2.5 expression in mouse ES cells over time, following treatment with DM from day 0 to day 1 of differentiation.
Figure 3D:
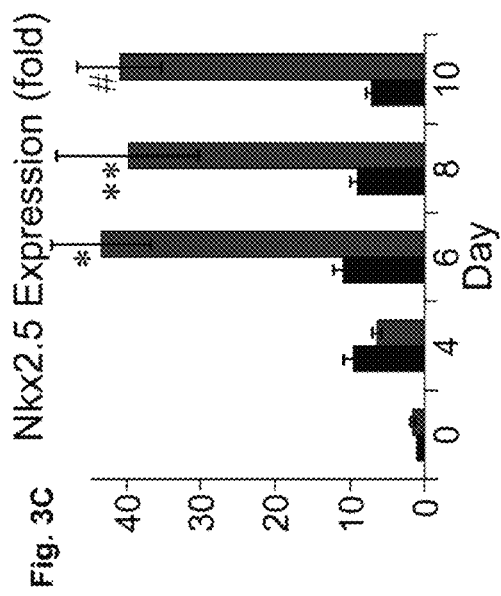
FIG. 3D is a bar graph depicting Myh6 expression in mouse ES cells over time, following treatment with DM from day 0 to day 1 of differentiation.

Effects of dorsomorphin treatment from day 0 to 1 of differentiation of EBs formed from hanging drops were examined further. This dorsomorphin-treatment protocol, which resulted in a 96.1% decrease in the BMP-response Id1 expression in comparison to DMSO control (FIG. 3A), led to substantial increases in beating areas, in comparison to DMSO controls. These increases were reflected in great increases in areas that immunostained for the cardiac-specific transcription factor Nkx2.5, and the sarcomeric protein alpha-actinin (FIG. 3B). As observed for the day −3 to 2 treatment, the 24-hour dorsomorphin treatment was associated with very large increases in the expression of cardiac-specific genes Nkx2.5 and Myh6, as measured by Q-PCR (up to 5.8-fold and 100-fold increases, respectively; FIGS. 3C and 3D).

Pharmacological BMP Inhibition Promotes Cardiomyogenesis at the Expense of Other Mesoderm-Derived Cell Lineages.

To gain insight into how dorsomorphin treatment promotes cardiomyogenesis, the expression of several markers of mesoderm-derived lineages in ES cells treated with 2 µM DM at day 0 to 1 was examined and compared to DMSO-treated cells. In contrast to the earlier finding with Noggin, which dramatically increased expression of the mesoderm marker Brachyury T (BryT) at day 3, dorsomorphin treatment (day 0 to 1) significantly reduced BryT expression at day 3 (FIG. 4A). However, with dorsomorphin treatment, significant levels of BryT expression persisted to day 4, when BryT expression was extinguished in controls (FIG. 4A). Dorsomorphin treatment caused even more striking changes to the expression of Mesp1, the earliest marker for cardiac precursor cells.[38] With dorsomorphin treatment, Mesp1 expression was nearly abolished at day 3, but a moderate level of Mesp1 expression was seen on day 4 (FIG. 4B). Thus, in a dramatic contrast to Noggin treatment or other reported manipulations that promote cardiomyogenesis in ES cells, dorsomorphin treatment does not simply increase overall expression of mesoderm makers per se, but rather delays the pattern of their expression.[3,4,5,39]

Interestingly, dorsomorphin treatment from day 0 to 1 dramatically decreased the expression of the hematopoietic progenitor marker Gata1 (FIG. 4C) and the smooth muscle-specific myosin heavy chain gene Myh11 (FIG. 4D). In addition, dorsomorphin treatment led to decreases in the expression of the vascular marker Flk-1 (Vegfr2) from day 3 to 8 (FIG. 4E). While Flk-1 expression is not endothelium-restricted[6], this result, together with the reduced vascular endothelial-cadherin (VE-Cad) expression at days 6 and 8 (FIG. 4F), suggests that dorsomorphin treatment decreases endothelial cell differentiation. Very similar results were seen for the day −3 to 2 dorsomorphin treatment (FIG. 5A-F). Thus, pharmacological blockade of BMP signaling during initial stages of ES cell differentiation promotes formation of pre-cardiac mesodermal cells at the expense of endothelial, smooth muscle, and hematopoietic lineages.

Discussion

Small molecules that selectively modulate important developmental pathways hold promise as versatile tools for dissecting signaling pathways involved in lineage commitment of pluripotent stem cells and for directing stem cell differentiation toward desired cell types.[3,4] Here, dorsomorphin, a recently described small molecule inhibitor of BMP signaling, has been used to reproducibly and substantially induce cardiomyogenesis in mouse ES cells. Dorsomorphin treatment during the first 24 hrs of differentiation was sufficient for robust cardiac induction, at the expense of other mesoderm-derived lineages.

These findings are generally in line with those obtained using the endogenous BMP antagonist Noggin,[5] however, several important differences are worth noting. First, whereas the Noggin treatment must begin prior to the initiation of EB formation for a total duration of 5 days to achieve efficient cardiomyogenesis, dorsomorphin treatment begun at the time of EB formation and continued for just 24 hours was able to induce cardiomyogenesis very efficiently (FIG. 2). Second, in contrast to Noggin, dorsomorphin treatment did not increase the peak expression of the mesoderm marker BryT at day 3 of differentiation; rather, it led to a much lower BryT expression at day 3, followed by a moderate residual expression at day 4, when BryT expression is normally extinguished (FIG. 4A). Effects of dorsomorphin treatment on Mesp1 expression is even more striking (FIG. 4B). Thus, in contrast to Noggin, dorsomorphin treatment does not appear to augment the overall formation of mesodermal cells (BryT+) or even early progenitor cells with cardiogenic potential (Mesp1+), but rather to commit the limited number of progenitor cells that do form under treatment conditions for cardiomyogenic development.

Together with increases in the expression of cardiac-specific genes and decreases in the expression of endothelial, smooth muscle and hematopoietic markers, dorsomorphin-induced delays in the temporal expression patterns of BryT and Mesp1 are consistent with a shift in the developmental repertoire of mesodermal cells toward the formation of cardiac precursor cells, which appear to arise after the formation of hemangioblastic population.[6,31] Dorsomorphin treatment during the first 24-hours of ES cell differentiation can increase the proportion of mesodermal cells that are committed to the cardiac lineage, consequently leaving less for endothelial, smooth muscle and hematopoietic development. Alternatively, cardiac induction can be a secondary consequence of blocking noncardiac development in multipotent progenitors. Collectively, these findings provide additional support for the interplay between the myocardial and the hemangioblast lineages as they diverge from a common progenitor,[6,40,41] and suggest that blocking BMP signaling during the initial stages of ES cell differentiation tips the balance in favor of cardiomyogenesis.

Distinct effects of Noggin and dorsomorphin on ES cell differentiation can reflect intrinsic differences between the small molecule dorsomorphin and protein-based antagonists. Dorsomorphin efficiently induces cardiomyogenesis when added at the onset of differentiation, whereas robust induction by Noggin is observed only when it is added prior to EB formation. This difference can reflect the small molecule's ability to readily penetrate multiple cell layers in developing EBs. In contrast, endogenous antagonists like Noggin cannot gain full access to cells once EB is formed. The differences could also arise from the fact that dorsomorphin appears to target multiple type-I BMP receptor subtypes,[34] whereas Noggin's effects may be limited to antagonizing a specific BMP ligand.

A selective small molecule inhibitor of the BMP signaling pathway, an important developmental pathway, has been utilized, as described herein, to greatly promote differentiation of pluripotent ES cells toward cardiac development Inherent advantages of small molecules like dorsomorphin could prove valuable for translation of recent stem cell advances into viable regenerative therapies. For example, dorsomorphin, which unlike endogenous BMP antagonists does not exhibit limited selectivity for ligand subtypes,[34] can expand empiric efforts to modulate stem cell differentiation even in contexts where the specific cocktail of active BMPs is unknown. Moreover, because dorsomorphin provides precise temporal control over BMP signaling, it was possible to pinpoint the critical time for cardiac induction to the initial 24-hours of ES cell differentiation. Such temporal control will prove to be critical for functional dissection of BMP signaling in complex biological contexts like organogenesis, where BMP signals function at multiple developmental nodes with often divergent effects. Finally, because small molecules in principle are relatively inexpensive, can penetrate many cell layers, and may be orally bioavailable, pharmacologic modulators of key developmental pathways will be useful, not just to control differentiation of pluripotent stem cells in vitro, but also to enhance the regenerative potential of resident stem cells in vivo.

Materials and Methods

Cell Culture

Murine ES cell lines, CGR8 and R1, were grown in feeder-free conditions as monolayers. The CGR8 ES cell line was transfected with the nuclear-localized red fluorescent protein (DsRed-Nuc) gene that was expressed under the cardiac α-myosin heavy chain promoter (the α-MHC promoter vector was kindly provided by J. Robbins and M. Anderson, and pDsRed-Nuc vector was purchased from Clontech). CGR8 cells were maintained in GMEM (Sigma-Aldrich) supplemented with 10% FBS (Gibco), 2 mM L-glutamine, (Cellgro), 0.05 mM 2-mercaptoethanol (Sigma-Aldrich), and 200 U/ml murine LIF (Chemicon International). R1 cells were maintained in High Glucose DMEM (Gibco) supplemented with 15% FBS, 2 mM L-glutamine, 1× nonessential amino acids, 100 U/ml penicillin-100 µg/ml streptomycin (Cellgro), 0.05 mM 2-mercaptoethanol, 1 mM sodium pyruvate (Sigma-Aldrich), and 200 U/ml murine LIF. Both cell lines were cultured on 0.2% gelatin-coated dishes. Every 24 hours, cells were washed in 1×PBS and culture media was replaced. Cells were passaged when confluence reached 50-60% to preserve the undifferentiated phenotype.

Initiation of Dorsomorphin Treatment

For experiments in which dorsomorphin treatment was begun prior to EB formation, ES cell cultures at 10% confluence were treated with ES media supplemented with 2 µM dorsomorphin (Compound C, Sigma-Aldrich) dissolved in DMSO (Sigma-Aldrich). Cells treated with media containing an equivalent amount of DMSO served as a negative control. ES media containing either dorsomorphin or DMSO was changed daily for three days.

ES cell Differentiation

After ES cell treatment with dorsomorphin or DMSO for three days (on Day 0), ES cells were trypsinized and embryoid bodies (EBs) were generated by the three-dimensional hanging drop method (Day 0). Briefly, EBs were grown in hanging drops for two days (Day 0 to Day 2), each of which initially consisted of 500 cells in 19 µL of EB differentiation media. The EB differentiation media was composed of IMDM (Gibco) supplemented with 20% FBS, 1.6 mM L-glutamine, 1× nonessential amino acids, 0.08 mM 2-mercaptoethanol, and either 2 µM dorsomorphin or DMSO. For R1 cells, differentiation media additionally contained 1 mM sodium pyruvate. At day 2 of differentiation (Day 2), treatment with dorsomorphin or DMSO was discontinued. The EBs were transferred to uncoated Petri dishes and suspended in differentiation media for two days (Day 2-Day 4). On Day 4, the EBs were moved to gelatin-coated 6-well plates, allowed to attach and incubated in differentiation media until Day 14. Throughout this time, the media was replaced every 48-72 hours. Each day, differentiating cell clusters were microscopically examined for the presence of contracting cardiomyocytes and, in the case of CGR8 cells, red fluorescence.

A second culture technique was used to form embryoid bodies (EB), which allowed for the quantification of the number of beating EBs. The ES cells were grown in accordance with the aforementioned methods. Rather than constructing hanging drops on day 0, aliquots of cells were distributed in uncoated 96-well round bottom plates, and 100 µL of dorsomorphin- or DMSO-containing differentiation media was added to each well. Beginning on day 2, the media was replaced every 48-72 hours with differentiation media lacking dorsomorphin or DMSO. EBs were microscopically examined for contracting cardiomyocytes on days 8 through 12. Any well containing spontaneously beating cells was recorded as 1 positive result.

For experiments in which dorsomorphin treatment was begun at the time of EB formation, EBs were generated by aforementioned methods in the presence of dorsomorphin or DMSO. At specified times, treatment with dorsomorphin or DMSO was discontinued.

Quantification of DAPI+ and DsRed+ Cells.

Embryoid bodies grown on gelatin-coated plates (Day 12) were stained with 5 µM 4'-6-Diamidino-2-phenylindole (DAPI) for 60 minutes. After washing out DAPI in EB media, images of DAPI+ nuclei and of DsRed+ nuclei within a 2.4× 2-mm field of view containing a distinct EB body were obtained. Numbers of DAPI+ and DsRed+ nuclei within a field of view were calculated using the Simple PCI automated image analysis program.

Immunostaining of Embryoid Bodies.

Cells from both dorsomorphin and DMSO-treated EBs were fixed at day 10 with 5% formaldehyde, and then permeabilized with 0.2% Triton X-100. After blocking with 1 mg/ml BSA, cells were incubated with mouse monoclonal α-actinin (Sigma) and goat Nkx2.5-2.5 (Santa Cruz) antibodies at concentrations recommended by the manufacturers. After overnight incubation, the cells were washed several times with PBS and then incubated with the appropriate secondary antibodies, either AlexaFluor-488 rabbit anti-mouse IgG (Molecular Probes) or Cy3 conjugated AffiniPure rabbit anti-goat IgG (Jackson Immuno). The immunostained stained cells were visualized using a Leica inverted microscope.

Quantitative Real-Time PCR

Cells were harvested on days 0, 2, 3, 4, 6, 8, 10, 12 of EB differentiation and stored at −80° C. in lysis buffer RLT (Qiagen). Three independent samples were collected for each time point studied. Total RNA was extracted using the RNeasy Mini Kit according to the manufacturer's instructions and treated with RNase-free DNase (Qiagen). First-strand cDNA was synthesized with the SuperScript III First-Strand Synthesis SuperMix for qRT-PCR (Invitrogen). Using cDNA as template, TaqMan real-time PCR assays was performed in triplicates on the ABI Prism 7900 HT sequence detection system (Applied Biosystems) according to the manufacturer's instructions. Data were normalized to GAPDH, and levels of gene expression were normalized to that of Day 0 DMSO-treated cells. The following TaqMan probe and primers sets (Applied Biosystems) were used: Id1 (Mm00775963_g1), nkx2.5 (Mm00657783_m1), myh6 (Mm00440354_m1), myl2 (Mm00440384_m1), brachyury T (Mm00436877_m1), flk-1 (Mm00440099_m1), myh11 (Mm00443013_m1), gata1 (Mm00484678_m1), ve-cadherin (Mm00486938_m1), mesp1 (Mm00801883_g1), and GAPDH (Mm99999915_g1).

Kinase Inhibition Studies.

Using staurosporin as a control, the compounds set forth in Table 3 were tested against various kinases to determine the kinase inhibition activity of each compound.

TABLE 3
Compounds Tested
| Compound ID | Structure |
|---|---|
| 1 | 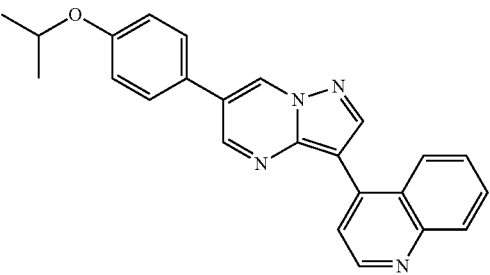 [SMILES: CC(C)Oc1ccc(-c2cnc3c(-c4ccnc5ccccc45)cnn3c2)cc1] |
| 2 | 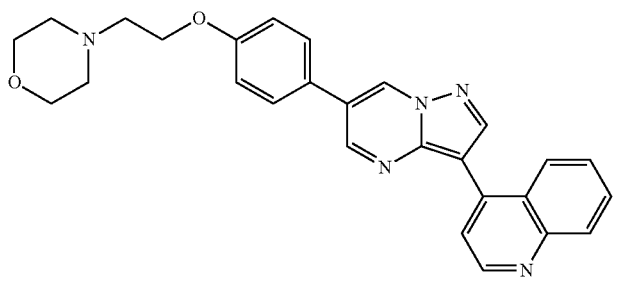 [SMILES: c1ccc2c(-c3cnn4cc(-c5ccc(OCCN6CCOCC6)cc5)cnc34)ccnc2c1] |
| 3 | 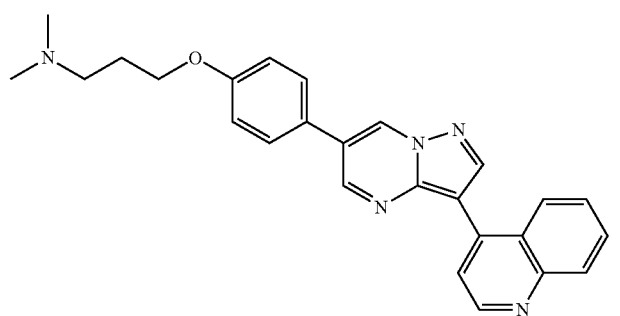 [SMILES: CN(C)CCCOc1ccc(-c2cnc3c(-c4ccnc5ccccc45)cnn3c2)cc1] |
| 4 | 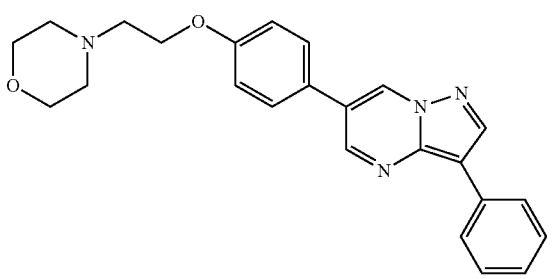 [SMILES: c1ccc(-c2cnn3cc(-c4ccc(OCCN5CCOCC5)cc4)cnc23)cc1] |
| 5 | 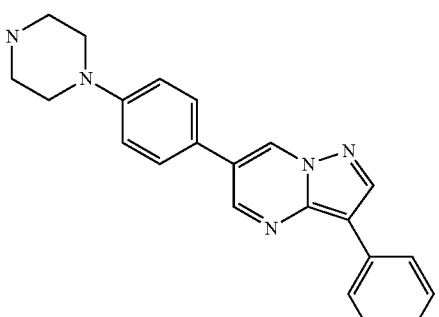 |

TABLE 3-continued

Compounds Tested

| Compound ID | Structure |
|---|---|
| Dorsomorphin (DM) | 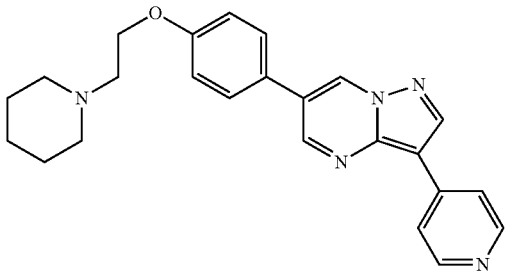 [SMILES: c1cc(-c2cnn3cc(-c4ccc(OCCN5CCCCC5)cc4)cnc23)ccn1] |

Kinase assays were performed using the assay kit by Reaction Biology Corp (Malvern, Pa.). The compounds were tested at 10 concentrations by 3-fold serial dilutions starting at 30 µM. Staurosporin was used as a control nonspecific kinase inhibitor. In vitro kinase reactions using purified kinases were carried out in the presence of 10 µM ATP and test compounds. IC50 (concentration producing 50% inhibition) for each compounds was determined, and the results are set forth in Table 4.

TABLE 4

IC50 (nM) of tested compounds inhibiting activity of identified kinases.

| | IC50 (nM) | | | |
|---|---|---|---|---|
| Compound ID | ALK2/ ACVR1 | ALK5/ TGFβ | AMPK | KDR/ VEGR2 |
| 1 | 107.90 | — | — | — |
| 2 | 42.77 | 1578.003 | 527.00 | 2418.00 |
| 3 | 26.68 | 998.99 | 1940.00 | 2062.00 |
| 4 | 2570.00 | — | 2916.00 | 234.50 |
| 5 | 40.72 | 565.00 | 1122.00 | 214.70 |
| Dorsomorphin | 148.10 | 10760.00 | 318.20 | 25.14 |
| Staurosporin | 4329.00 | 8385.00 | <1.0 | 3.29 |

The in vitro kinase results indicate that Compounds 1, 2 and 3 had significantly diminished KDR and AMPK inhibitor activity compared to dorsomorphin. In fact, Compound 1 is particularly specific for ALK2 without any detectible inhibition of KDR, AMPK, and ALK5. BMP inhibitors with greater selectivity and less "off target activities" are inherently more valuable as signaling modulators and therapeutics.

Studies on Directed Differentiation of Human Embryonic Stem (ES) Cell Studies.

The present inventors have developed an efficient protocol to direct cardiac differentiation of human pluripotent stem cells in precisely defined steps designed to minimize variability. The centerpiece of this approach is the use of a small molecule modulator of developmental pathways (FIG. 7), which permits a precise control of differentiation of human ES cells.

Figure 7:
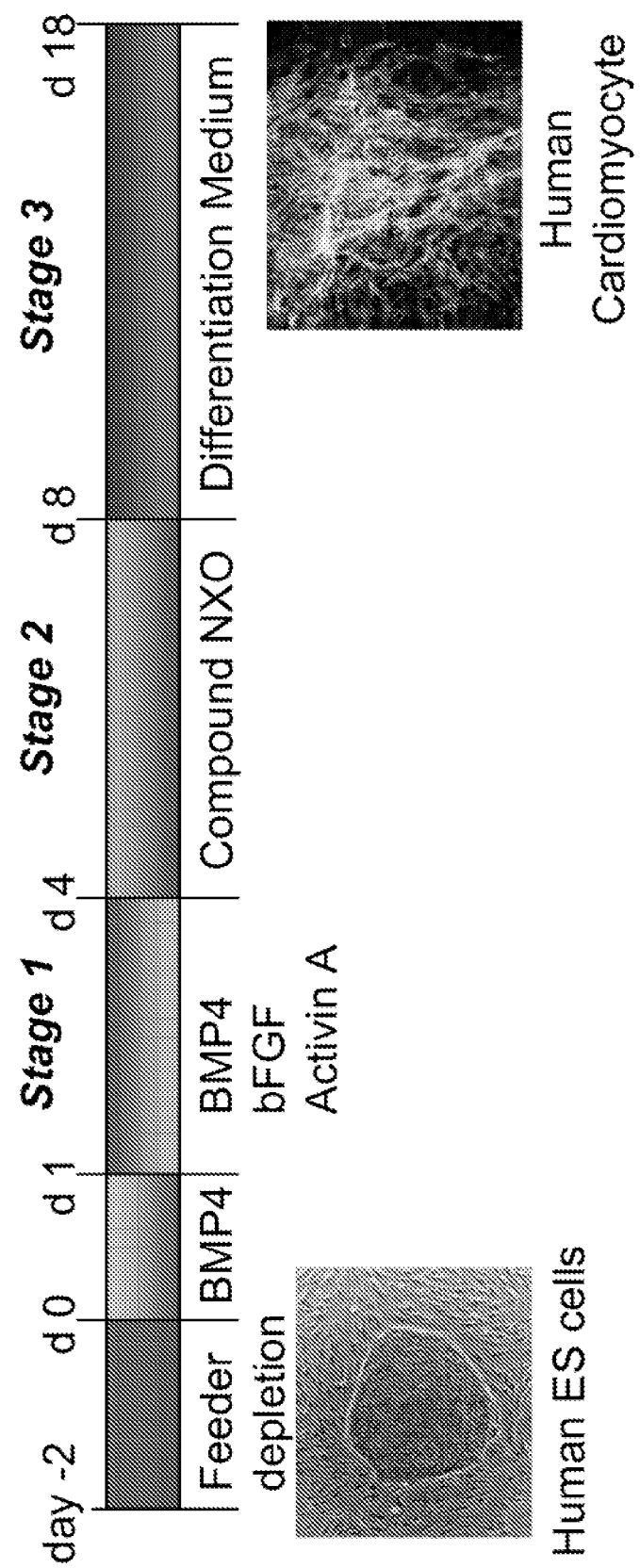
FIG. 7 is a graphical depiction of a protocol for recapitulating stages of cardiomyogenesis during embryongenesis.
Figure 8A:
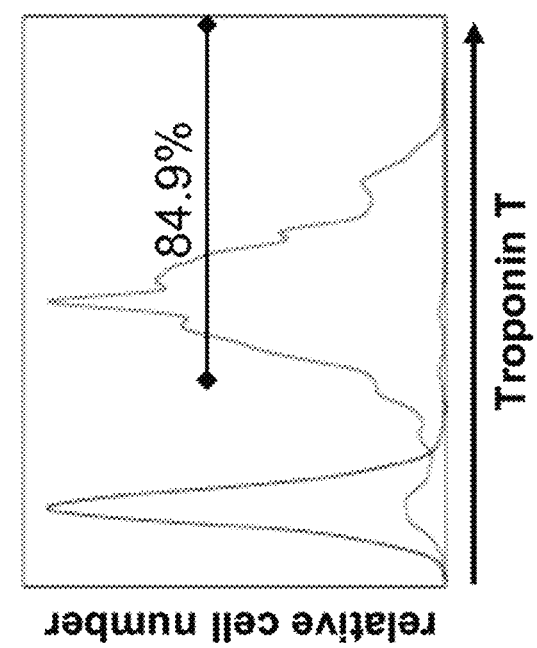
FIG. 8A includes the results of a flow cytometry study 18 days after differentiation using a cardiac specific Troponin T antibody, distinguishing traditional approach without cytokines in serum-free conditions, and directed differentiation.
Figure 8B:
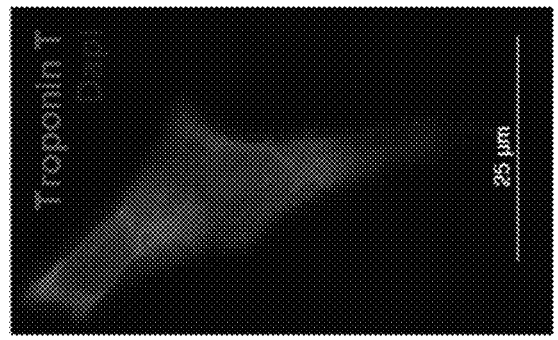
FIG. 8B includes the results of a fluorescence immunohistochemistry study of cultured hES cell 14 days after differentiation showing expression of cardiac troponin T.

Based on the understanding that stage-specific inhibition of the canonical WNT signaling is required for cardiac development (Yang et al, 2008), the present inventors devised a chemical-based approach to promote cardiac development in human ES cells that bypasses the requirement for WNT inhibitor Dickkopf homolog 1 (DKK1) (FIG. 7). This chemical-based approach should overcome the variability and the expense of using DKK1, permitting scaled-up production of cardiomyocytes necessary for large-scale molecular profiling or eventual cell-based therapies.

To direct the differentiation of human ES cells to the cardiac lineage, the present inventors have developed a protocol that attempts to recapitulate stages of cardiomyogenesis during embryogenesis: the formation of primitive streak (stage 1), the specification of cardiac mesoderm (stage 2), and the differentiation of functional cardiomyocytes (stage 3) (Yang et al, 2008). In the initial steps of cardiac induction, cells are sequentially exposed to growth factors as previously described for human ES cells, but at day 4 (stage 2), DKK1 and VEGF are substituted with Compound 1 (Table 3), DM-3189, and Dorsomorphin, which can stimulate cardiomyogenesis in human ES cells in the absence of DKK1. The precise mechanism by which dorsomorphin and its structural analogs induce cardiomyogenesis is unknown, but preliminary expression profile experiments suggest that the canonical Wnt signaling is markedly decreased in treated ES cells (Table 5).

TABLE 5

Small molecule BMP inhibitor administration leads to substantial decreases in expression of Wnt signaling components in ES cells. Comparative microarray expression data of ES cells treated with Compound I or DMSO for 2 days.

| Gene | Rel. Expresn. (NXO vs DMSO) | Comments |
|---|---|---|
| Wnt8a | 0.16217 | Wnt ligand |
| Fst | 0.17985 | Wnt responsive expression [1] |
| Axin2 | 0.25086 | Wnt pathway negative feedback, Wnt responsive [2] |
| Sp5 | 0.35569 | Wnt responsive expression [4] |
| Mixl1 | 0.35995 | Wnt responsive expression [5] |
| Fgf8 | 0.36155 | Wnt responsive expression [8] |
| R-spondin 3 | 0.36234 | Wnt pathway activator [9] |
| Cadherin-11 | 0.37846 | Wnt responsive expression [10] |
| Evx1 | 0.37886 | Wnt responsive expression [5] |
| Wnt3 | 0.38024 | Wnt ligand |
| GPR177 (Wntless family) | 0.38462 | Wnt pathway mediator [11] |

Cardiomyocyte differentiation was conducted as described by Yang and his colleagues. Two days prior to the initiation of differentiation, human ES cells, which were maintained in MEF feeder cells, were plated on Matrigel. To generate EBs, human ES cells are dissociate into small 10-20 cell clusters and plated on ultra-low attachment plates (Corning) in 2 mL aggregation media (StemPro-34 (Invitrogen) supplemented with penicillin/streptomycin, 2 mM glutamine, 0.4 mM monothioglycerol, 50 µg/ml ascorbic acid, and 0.5 ng/ml BMP-4 (Yang et al., 2008; Kennedy et al., 2007). On day 1-4 of differentiation (stage 1), BMP concentration is increased to 10 ng/mL and bFGF (5 ng/mL) and activin A (3 ng/mL) added. On day 4 (stages 2), BMP-4, bFGF and activin A are removed, and Compound I (0.5 µM), dorsomorphin (2 µM), or other small molecule BMP inhibitors added. At day 8, to promote cardiac differentiation (stage 3), EBs are transferred to 0.1% gelatin-coated dishes and cultured in EB20 cardiac differentiation medium (DMEM supplemented with 20% fetal bovine serum and 1 mM L-glutamine, 0.1 mM β-mercaptoethanol, 1% nonessential amino acids, GIBCO) (Zhang et al., 2009). In this medium, beating human ES cell derived-cardiomyocytes can be maintained up to 100 days. By day 10, a large majority (>95%) of cells will start beating spontaneously, and by day 18, over 80% of cultured cells will express cardiac Troponin T by FACS analysis and immunohistochemistry (Figure XI). By comparison, in the absence of cytokines and small molecules to direct differentiation toward cardiomyocytic lineages, the yield of cardiomyogenesis appears negligible. Typically, human ES cell lines produce 10 to 25% of embryoid bodies (EBs) that beat spontaneously and human iPS cell lines produce only 5 to 10% of EBs that beat (Zhang, et al., 2009). Additionally, under these conditions, only 2-5% of cells within beating EBs express cardiac markers (Cao, et al, 2008). Thus, traditional methods to generate human cardiac cells from ES and iPS cells are far too inefficient, and the methods and reagents discussed in this manuscript overcomes these major.

The significance of this approach is that human pluripotent stem cells, such as human embryonic stem (ES) cells and patient-derived human induced pluripotent stem (iPS) cells can now be efficiently directed toward cardiac cell types in vitro using small molecules. Thus, in principle, small molecule inhibitors of BMP signaling, like Compound 1-5, and DM, can be used as pharmaceutical agents to direct differentiation of pluripotent stem cells cardiomyocytes and other desired cell types, and to promote regenerative processes in the body to replace damaged tissues.

Because stem cell maintenance and differentiation utilize the same key intercellular signaling networks that regulate embryonic development, ability to precisely control these developmental pathways is a promising approach to achieve directed stem cell differentiation and to boost body's endogenous regenerative capacity. For example, timely inhibition of BMP signaling using endogenous BMP antagonist noggin is effective for achieving directed differentiation of pluripotent stem cells to cardiomyocytes and neurons (Hao, et al., 2008; Yuasa, et al, 2007; Chambers, et al., 2009; Cohen, et al., 2007).

Small molecule BMP inhibitors like Compounds I-5, and dorsomorphin will prove to be valuable tools for regenerative medicine. An important advantage of small molecules over decoy BMP receptors, endogenous BMP antagonists, and neutralizing antibodies, in the context of differentiating embryoid bodies (EB) cells formed by differentiating embryonic (ES) cells, is that small molecules are easily accessible to cells at the center of EB clusters. Hence, signal modulation is uniform within each EB, affording consistent results over protein-based inhibitors, which need to be administered at high concentrations to be effective. Plus, small molecules are much less expensive than recombinant proteins, affording scaling up of various differentiation protocols. For use in whole live animals or patients, the advantage of a small molecule BMP inhibitor is even more dramatic. Small molecule BMP inhibitor can be delivered to living organisms inexpensively. By contrast, recombinant endogenous BMP antagonist such as noggin would be prohibitively expensive to administer to live animals, requiring the intravenous dosing of gram quantities of protein. Ultimately, small molecule BMP inhibitors may be routinely used not only to expand specific tissue types in vitro, but also be used to enhance appropriate differentiation of transplanted stem cells or endogenous progenitors in human patients. In conclusion, small molecule cell signaling modulators like compounds I-5, and dorsomorphin will be useful for a successful translation of recent stem cell advances into viable therapeutic modalities.

It will be understood that various details of the presently-disclosed subject matter can be changed without departing from the scope of the subject matter disclosed herein. Furthermore, the foregoing description is for the purpose of illustration only, and not for the purpose of limitation.

Throughout this document, various references are mentioned. All such references are incorporated herein by reference, including the references set forth in the following list:

REFERENCES

1. Fukuda K, Yuasa S. Stem Cells as a source of regenerative cardiomyocytes. Circ. Res. 98:1002-1013 (2006).
2. Laflamme M A, Chen K Y, Naumova A V, Muskheli V, Fugate J A, et al. Cardiomyocytes derived from human embryonic stem cells in pro-survival factors enhance function of infarcted rat hearts. Nat Biotechnol 25: 1015 (2007).
3. Ueno S, Weidinger G, Osugi T, Kohn A D, Golob J L, et al. Biphasic role for Wnt/beta-catenin signaling in cardiac specification in zebrafish and embryonic stem cells. Proc Natl Acad Sci USA 104: 9685-9690 (2007).
4. Naito A T, Shiojima I, Akazawa H, Hidaka K, Morisaki T, et al. Developmental stage-specific biphasic roles of Wnt/beta-catenin signaling in cardiomyogenesis and hematopoiesis. Proc Natl Acad Sci USA 103: 19812-19817 (2006).
5. Yuasa S, Itabashi Y, Koshimizu U, Tanaka T, Sugimura K, et al. Transient inhibition of BMP signaling by Noggin induces cardiomyocyte differentiation of mouse embryonic stem cells. Nat Biotechnol 23: 607-611 (2005).
6. Kattman S J, Huber T L, Keller G M. Multipotent flk-1+ cardiovascular progenitor cells give rise to the cardiomyocyte, endothelial, and vascular smooth muscle lineages. Dev Cell 11: 723-732 (2006).
7. Kitisin K, Saha T, Blake T, Golestaneh N, Deng M, et al. Tgf-Beta signaling in development. Sci STKE 2007: cm1 (2007).
8. Boyle A J, Schulman S P, Hare J M, Oettgen P. Is stem cell therapy ready for patients? Stem Cell Therapy for Cardiac Repair. Ready for the Next Step. Circulation 114: 339-352 (2006).
9. Hsieh P C, Segers V F, Davis M E, MacGillivray C, Gannon J, et al. Evidence from a genetic fate-mapping study that stem cells refresh adult mammalian cardiomyocytes after injury. Nat Med 13: 970-974 (2007).
10. Beltrami A P, Barlucchi L, Torella D, Baker M, Limana F, et al. Adult cardiac stem cells are multipotent and support myocardial regeneration. Cell 114: 763-776 (2003).
11. Ellison G M, Torella D, Karakikes I, Nadal-Ginard B Myocyte death and renewal: modern concepts of cardiac cellular homeostasis. Nat Clin Pract Cardiovasc Med 4 Suppl 1: S52-59 (2007).
12. Torella D, Ellison G M, Karakikes I, Nadal-Ginard B. Resident cardiac stem cells. Cell Mol Life Sci 64: 661-673 (2007).

13. Cingolani E, Ramirez Correa G A, Kizana E, Murata M, Cho H C, et al. Gene therapy to inhibit the calcium channel beta subunit: physiological consequences and pathophysiological effects in models of cardiac hypertrophy. Circ Res 101: 166-175 (2007).
14. Mendez-Ferrer S, Ellison G M, Torella D, Nadal-Ginard B. Resident progenitors and bone marrow stem cells in myocardial renewal and repair. Nat Clin Pract Cardiovasc Med 3 Suppl 1: S83-89 (2006).
15. Orlic D, Kajstura J, Chimenti S, Jakoniuk I, Anderson S M, et al. Bone marrow cells regenerate infarcted myocardium. Nature 410: 701-705 (2001).
16. Orlic D, Kajstura J, Chimenti S, Limana F, Jakoniuk I, et al. Mobilized bone marrow cells repair the infarcted heart, improving function and survival. Proc Natl Acad Sci USA 98: 10344-10349 (2001).
17. Wollert K C, Meyer G P, Lotz J, Ringes-Lichtenberg S, Lippolt P, et al. Intracoronary autologous bone-marrow cell transfer after myocardial infarction: the BOOST randomised controlled clinical trial. Lancet 364: 141-148 (2004).
18. Assmus B, Schachinger V, Teupe C, Britten M, Lehmann R, et al. Transplantation of Progenitor Cells and Regeneration Enhancement in Acute Myocardial Infarction (TOPCARE-AMI). Circulation 106: 3009-3017 (2002).
19. Janssens S, Dubois C, Bogaert J, Theunissen K, Deroose C, et al. Autologous bone marrow-derived stem-cell transfer in patients with ST-segment elevation myocardial infarction: double-blind, randomised controlled trial. Lancet 367: 113-121 (2006).
20. Chen S L, Fang W W, Ye F, Liu Y H, Qian J, et al. Effect on left ventricular function of intracoronary transplantation of autologous bone marrow mesenchymal stem cell in patients with acute myocardial infarction. Am J Cardiol 94: 92-95 (2004).
21. Rosenzweig A. Cardiac cell therapy—mixed results from mixed cells. N Engl J Med 355: 1274-1277 (2006).
22. Nadal-Ginard B, Fuster V. Myocardial cell therapy at the crossroads. Nat Clin Pract Cardiovasc Med 4: 1 (2007).
23. Oettgen P, Boyle A J, Schulman S P, Hare J M. Cardiac Stem Cell Therapy. Need for Optimization of Efficacy and Safety Monitoring. Circulation 114: 353-358 (2006).
24. Menasche P. Stem cells for clinical use in cardiovascular medicine: current limitations and future perspectives. Thromb Haemost 94: 697-701 (2005).
25. Menasche P. The potential of embryonic stem cells to treat heart disease. Curr Opin Mol Ther 7: 293-299 (2005).
26. Hodgson D M, Behfar A, Zingman L V, Kane G C, Perez-Terzic C, et al. Stable benefit of embryonic stem cell therapy in myocardial infarction. Am J Physiol Heart Circ Physiol 287: H471-479 (2004).
27. Kehat I, Kenyagin-Karsenti D, Snir M, Segev H, Amit M, et al. Human embryonic stem cells can differentiate into myocytes with structural and functional properties of cardiomyocytes. J Clin Invest 108: 407-414 (2001).
28. Caspi O, Huber I, Kehat I, Habib M, Arbel G, et al. Transplantation of human embryonic stem cell-derived cardiomyocytes improves myocardial performance in infarcted rat hearts. J Am Coll Cardiol 50: 1884-1893 (2007).
29. Kolossov E, Bostani T, Roell W, Breitbach M, Pillekamp F, et al. Engraftment of engineered ES cell-derived cardiomyocytes but not BM cells restores contractile function to the infarcted myocardium. J Exp Med 203: 2315-2327 (2006).
30. Singla D K, Hacker T A, Ma L, Douglas P S, Sullivan R, et al. Transplantation of embryonic stem cells into the infarcted mouse heart: formation of multiple cell types. J Mol Cell Cardiol 40: 195-200 (2006).
31. Kouskoff V, Lacaud G, Schwantz S, Fehling H J, Keller G. Sequential development of hematopoietic and cardiac mesoderm during embryonic stem cell differentiation. Proc Natl Acad Sci USA 102: 13170-13175 (2005).
32. Wu X, Ding S, Ding Q, Gray N S, Schultz P G. Small molecules that induce cardiomyogenesis in embryonic stem cells. J Am Chem Soc 126: 1590-1591 (2004).
33. Behfar A, Perez-Terzic C, Faustino R S, Arrell D K, Hodgson D M, et al. Cardiopoietic programming of embryonic stem cells for tumor-free heart repair. J Exp Med 204: 405-420 (2007).
34. Yu P B, Hong C C, Sachidanandan C, Babitt J L, Deng D Y, Hoyng S A, Lin H Y, Bloch K D, Peterson R T. Dorsomorphin inhibits BMP signals required for embryogenesis and iron metabolism. Nat. Chem. Biol. 4(1): 33-41 (2008).
35. Zhou G, Myers R, Li Y, Chen Y, Shen X, et al. Role of AMP-activated protein kinase in mechanism of metformin action. J Clin Invest 108:1167-1174 (2001).
36. Palermo J, Gulick J, Colbert M, Fewell J, Robbins J. Transgenic remodeling of the contractile apparatus in the mammalian heart. Circ. Res. 78: 504-509 (1996).
37. Ying Q L, Nichols J, Chambers I, Smith A. BMP induction of Id proteins suppresses differentiation and sustains embryonic stem cell self-renewal in collaboration with STAT3. Cell 115: 281-292 (2003).
38. Saga Y, Miyagawa-Tomita S, Takagi A, Kitajima S, Miyazaki J, et al. MesP1 is expressed in the heart precursor cells and required for the formation of a single heart tube. Development 126: 3437-3447 (1999).
39. Liu Y, Asakura M, Inoue H, Nakamura T, Sano M, et al. Sox17 is essential for the specification of cardiac mesoderm in embryonic stem cells. Proc Natl Acad Sci USA 104:3859-3864 (2007).
40. Schoenebeck J J, Keegan B R, Yelon D. Vessel and blood specification override cardiac potential in anterior mesoderm. Dev Cell 13:254-267 (2007).
41. Moretti A, Caron L, Nakano A, Lam J T, Bernshausen A, et al. Multipotent embryonic isl1+ progenitor cells lead to cardiac, smooth muscle, and endothelial cell diversification. Cell 127: 1151-1165 (2006).
42. Hao, J., Daleo, M. A., Murphy, C. K., Yu, P. B., Ho, J. N., Hu, J., Peterson, R. T., Hatzopoulos, A. K., Hong, C. C. Dorsomorphin, a selective small molecule inhibitor of BMP signaling, proposes cardiomyogenesis in embryonic stem cells.
43. Yang, L., et al., Human cardiovascular progenitor cells develop from a KDR+ embryonic-stem-cell-derived population. Nature, 2008. 453(7194): p. 524-8.
44. Zhang, J., et al., Functional cardiomyocytes derived from human induced pluripotent stem cells. Circ Res, 2009. 104(4): p. e30-41.
45. Kennedy, M., et al., Development of the hemangioblast defines the onset of hematopoiesis in human ES cell differentiation cultures. Blood, 2007. 109(7): p. 2679-87.
46. Cao, F., et al., Transcriptional and functional profiling of human embryonic stem cell-derived cardiomyocytes. PLoS ONE, 2008. 3(10): p. e3474.
47. Yuasa, S., et al., Transient inhibition of BMP signaling by Noggin induces cardiomyocyte differentiation of mouse embryonic stem cells. Nat Biotechnol, 2005. 23(5): p. 607-11.
48. Chambers, S. M., et al., Highly efficient neural conversion of human ES and iPS cells by dual inhibition of SMAD signaling. Nat Biotechnol, 2009. 27(3): p. 275-80.

49. Cohen, M. A., P. Itsykson, and B. E. Reubinoff, Neural differentiation of human ES cells. Curr Protoc Cell Biol, 2007. Chapter 23: p. Unit 23 7.

What is claimed is:

1. A compound of the formula:

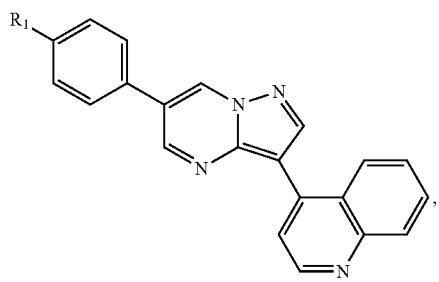

wherein $R_1$ is selected from the group consisting of

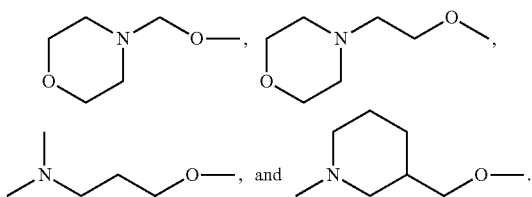

2. The compound according to claim 1 of the formula:

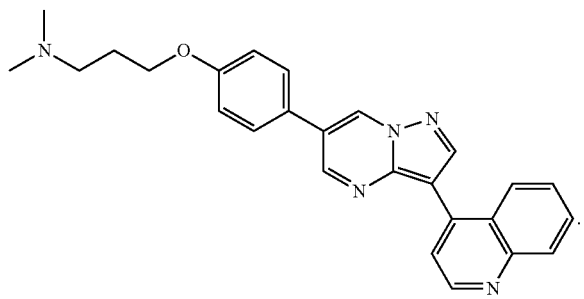 [SMILES: CN(C)CCCOc1ccc(-c2cnc3c(-c4ccnc5ccccc45)cnn3c2)cc1]

3. The compound according to claim 1 of the formula:

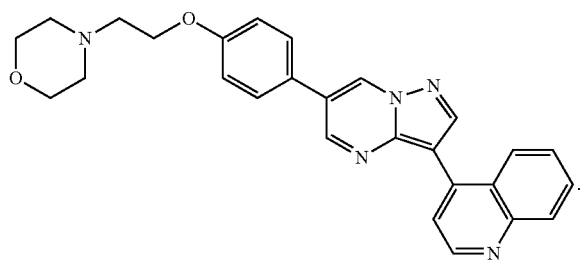 [SMILES: c1ccc2c(-c3cnn4cc(-c5ccc(OCCN6CCOCC6)cc5)cnc34)ccnc2c1]

4. A method of selectively differentiating a stem cell, comprising:
providing the stem cell; and
contacting the stem cell with an effective amount of a compound of the formula,

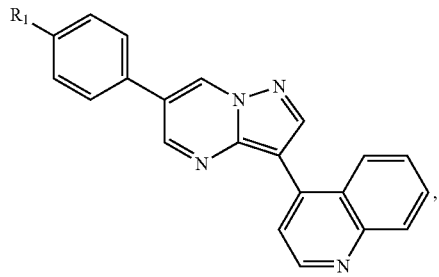

wherein $R_1$ is selected from the group consisting of

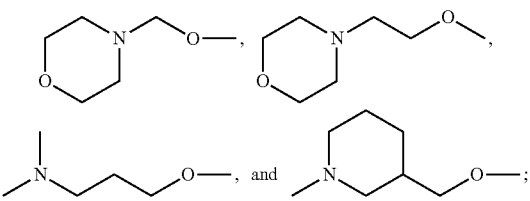

and
wherein the stem cell becomes differentiated into a cardiomyocyte.

5. The method of claim 4, wherein the compound is

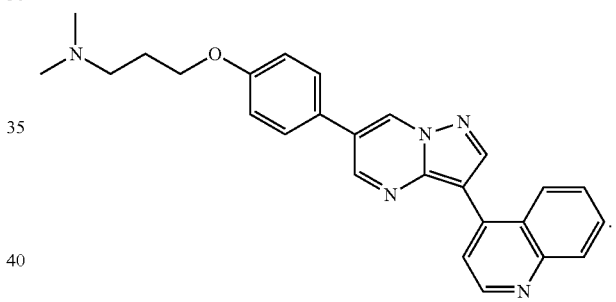

6. The method of claim 4, wherein the compound is

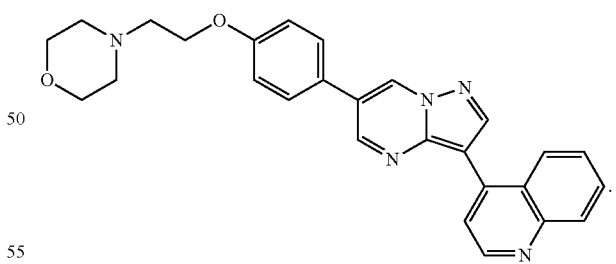

7. The method of claim 4, wherein the compound is an inhibitor of Bone Morphogenetic Protein (BMP) signaling.

8. The method of claim 4, wherein contacting the cells with the compound causes the cells to exhibit at least one indicator of cardiomyogenesis.

9. The method of claim 8, wherein the at least one indicator of cardiomyogenesis is selected from: fluorescence, beating cells, and expression of at least one cardiac-specific gene.

10. The method of claim 9, wherein the at least one cardiac-specific gene is selected from: Nkx2.5, Troponin T, Myh6, Myl2, Myl7, and Mybpc3.

11. The method of claim 9, wherein the at least one indicator of cardiomyogenesis is beating cells and, the beating cells are first observed from about day 6 to about day 12.

12. The method of claim 4, further comprising:
providing a second compound that enhances terminal differentiation of committed cardiac progenitor cells; and
contacting the stem cell with the second compound.

13. The method of claim 4, wherein the stem cell is an embryonic stem cell.

14. The method of claim 4, wherein the stem cell is a human embryonic stem cell.

15. A method of screening for a compound useful for enhancing terminal differentiation of committed cardiac progenitor cells, comprising:
providing a first pluripotent stem cell and a second pluripotent stem cell;
contacting the first and second pluripotent stem cells with an effective amount of a first compound of the formula,

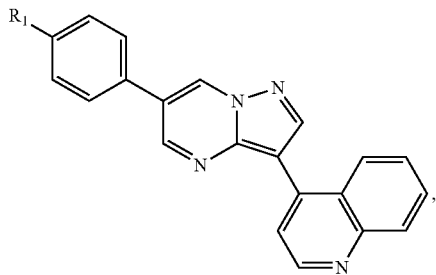

wherein $R_1$ is selected from the group consisting of

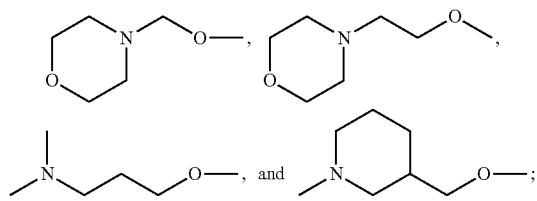

contacting the second cells with a test compound;
identifying at least one indicator of cardiomyogenesis exhibited by the first cells and the second cells;
comparing the appearance of the at least one indicator of cardiomyogenesis exhibited by the first cells to the appearance of the at least one indicator of cardiomyogenesis exhibited by the second cells; and
identifying the test compound as a compound useful for enhancing terminal differentiation of committed cardiac progenitor cells if the appearance of the at least one indicator of cardiomyogenesis in the second cells is accelerated and/or augmented as compared to the appearance of the at least one indicator of cardiomyogenesis in the first cells.

16. The method of claim 15, wherein the first compound is an inhibitor of Bone Morphogenetic Protein (BMP) signaling.

* * * * *